(12) United States Patent
Sweeney

(10) Patent No.: US 10,029,103 B2
(45) Date of Patent: Jul. 24, 2018

(54) SYSTEM AND METHOD FOR AUTOMATED ADJUSTMENT OF CARDIAC RESYNCHRONIZATION THERAPY CONTROL PARAMETERS

(75) Inventor: Michael O. Sweeney, Newton, MA (US)

(73) Assignee: THE BRIGHAM AND WOMEN'S HOSPITAL, Boston, MA (US)

( * ) Notice: Subject to any disclaimer, the term of this patent is extended or adjusted under 35 U.S.C. 154(b) by 522 days.

(21) Appl. No.: 14/131,868

(22) PCT Filed: Jul. 16, 2012

(86) PCT No.: PCT/US2012/046907
§ 371 (c)(1),
(2), (4) Date: Apr. 17, 2014

(87) PCT Pub. No.: WO2013/010165
PCT Pub. Date: Jan. 17, 2013

(65) Prior Publication Data
US 2014/0222099 A1  Aug. 7, 2014

Related U.S. Application Data

(60) Provisional application No. 61/507,760, filed on Jul. 14, 2011.

(51) Int. Cl.
*A61B 5/05* (2006.01)
*A61N 1/365* (2006.01)
(Continued)

(52) U.S. Cl.
CPC ........ *A61N 1/36592* (2013.01); *A61B 5/0472* (2013.01); *A61N 1/365* (2013.01); *A61N 1/3682* (2013.01)

(58) Field of Classification Search
CPC .. A61N 1/3627; A61N 1/365; A61N 1/36592; A61N 1/3682; A61N 1/3684; A61B 5/0472
(Continued)

(56) References Cited

U.S. PATENT DOCUMENTS 6,934,586 B2  8/2005  Struble et al.
7,096,064 B2  8/2006  Deno et al.
(Continued)

OTHER PUBLICATIONS

Sweeney, et al., Analysis of Ventricular Activation Using Surface Electrocardiography to Predict Left Ventricular Reverse Volumetric Remodeling During Cardiac Resynchronization Therapy, Circulation, 2010, 121:626-634.
(Continued)

*Primary Examiner* — Carl H Layno
*Assistant Examiner* — Jon Eric C Morales
(74) *Attorney, Agent, or Firm* — Quarles and Brady LLP

(57) ABSTRACT

A system and method for cardiac resynchronization therapy ("CRT") in which a model of baseline cardiac electrical activity, such as a model of global baseline cardiac electrical activity derived from various surface electrocardiograph ("ECG") signals, is utilized to automatically adjust pacing control parameters of a cardiac implantable electrical device ("CIED") are provided. The baseline model is compared to CRT response patterns using modified pacing control parameters in an iterative fashion, based on a patient-specific response pattern phenotype determination, until ventricular electrical asynchrony is minimized. The pacing control parameters resulting in the minimum ventricular electrical asynchrony are used to generate final control parameters for CRT.

18 Claims, 21 Drawing Sheets

(51) Int. Cl.
*A61B 5/0472* (2006.01)
*A61N 1/368* (2006.01)

(58) Field of Classification Search
USPC .......................................................... 607/25
See application file for complete search history.

(56) References Cited

U.S. PATENT DOCUMENTS

| | | |
|---|---|---|
| 7,555,336 B2 | 6/2009 | Sheth et al. |
| 2004/0122479 A1 | 6/2004 | Spinellli et al. |
| 2004/0172079 A1 | 9/2004 | Chinchoy |
| 2004/0193223 A1 | 9/2004 | Kramer et al. |
| 2004/0215252 A1 | 10/2004 | Verbeek et al. |
| 2006/0235478 A1 | 10/2006 | Van Gelder et al. |
| 2007/0142871 A1 | 6/2007 | Libbus et al. |
| 2008/0119903 A1* | 5/2008 | Arcot-Krishnamurthy .. A61B 5/04011 607/17 |
| 2008/0306568 A1 | 12/2008 | Ding et al. |
| 2009/0157134 A1 | 6/2009 | Ziglio et al. |
| 2009/0299423 A1 | 12/2009 | Min |
| 2010/0087888 A1 | 4/2010 | Maskara |
| 2010/0268059 A1* | 10/2010 | Ryu ....................... A61B 5/042 600/407 |

OTHER PUBLICATIONS

PCT International Search Report and Written Opinion, PCT/US2010/042337, dated Mar. 31, 2011, 10 pages.
PCT International Search Report and Written Opinion, PCT/US2012/023256, dated Aug. 27, 2012, 10 pages.
PCT International Search Report and Written Opinion, PCT/US2012/046907, dated Oct. 18, 2012, 7 pages.
Fung, et al., Chapter 20, Optimization of Cardiac Resynchronization Therapy, Cardiac Resynchronization Therapy, Second Edition, Copyright 2008 Blackwell Publishing Ltd., pp. 356-373.
Sweeney, et al., QRS Fusion Complex Analysis Using Wave Interference to Predict Reverse Remodeling During Cardiac Resynchronization Therapy, Heart Rhythm, 2014, 11:806-813.
European Patent Office, Supplementary European Search Report, Application No. EP 12811723, dated Mar. 4, 2015.

* cited by examiner

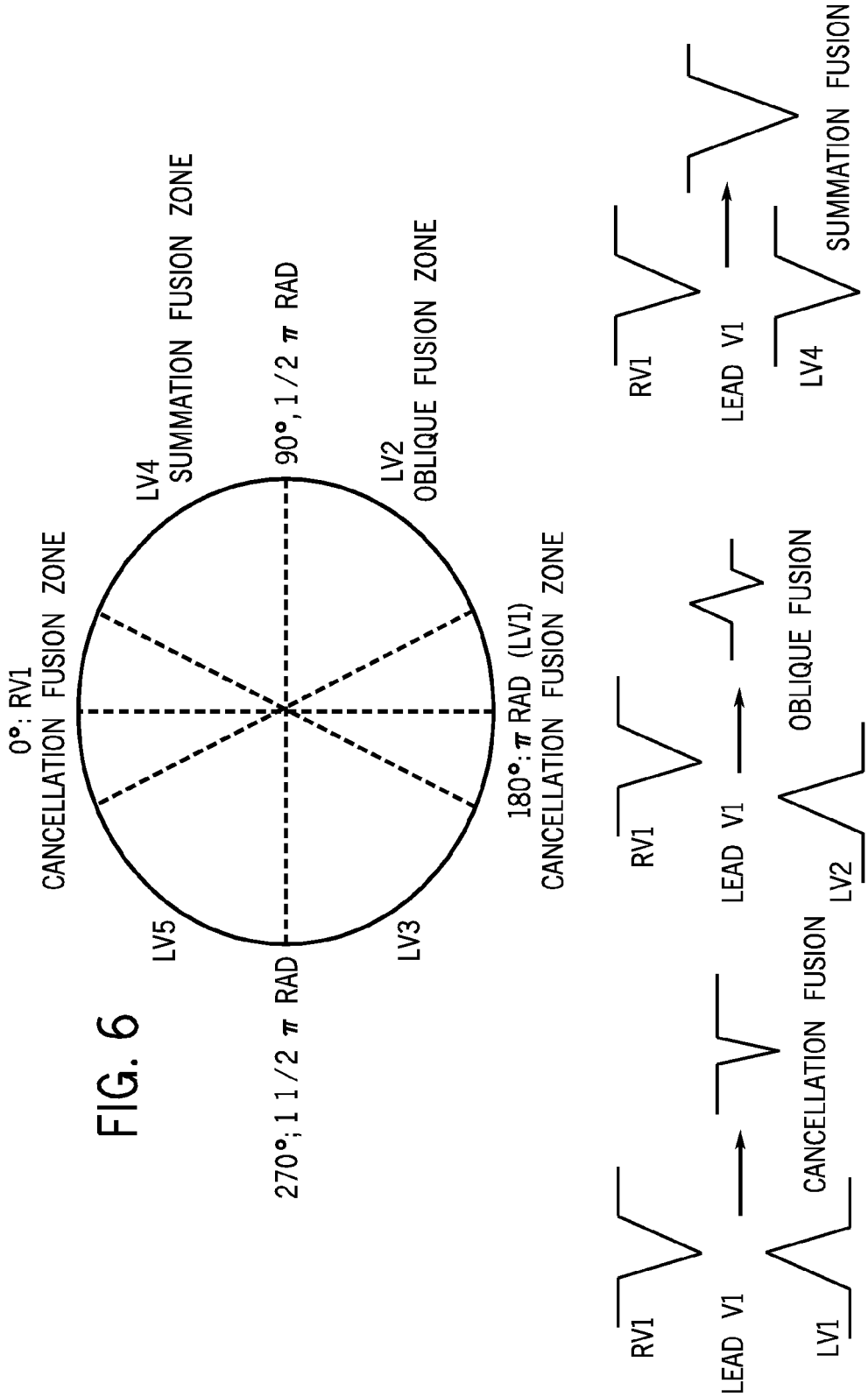

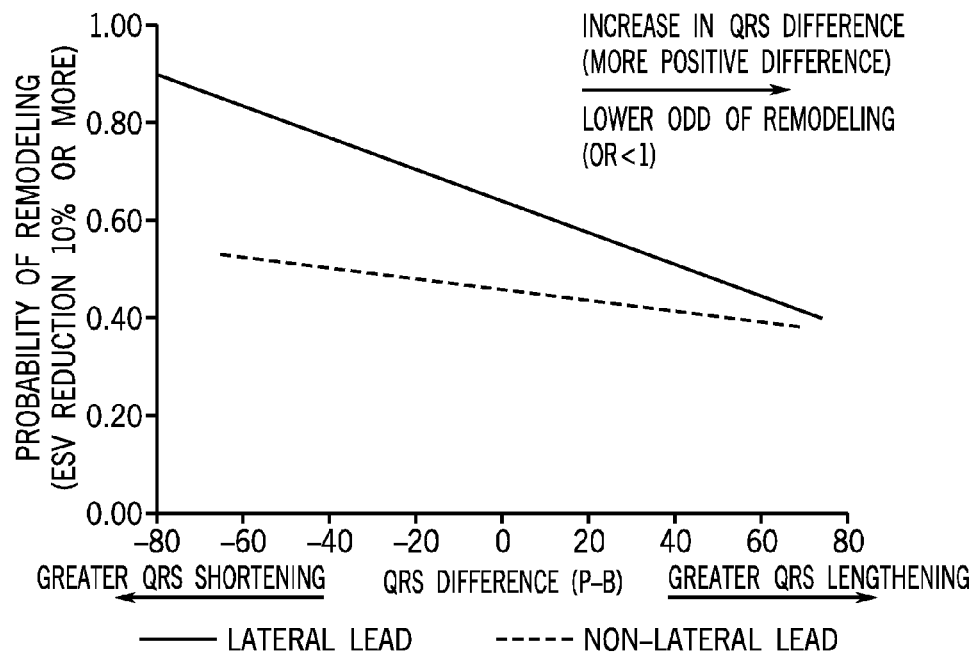
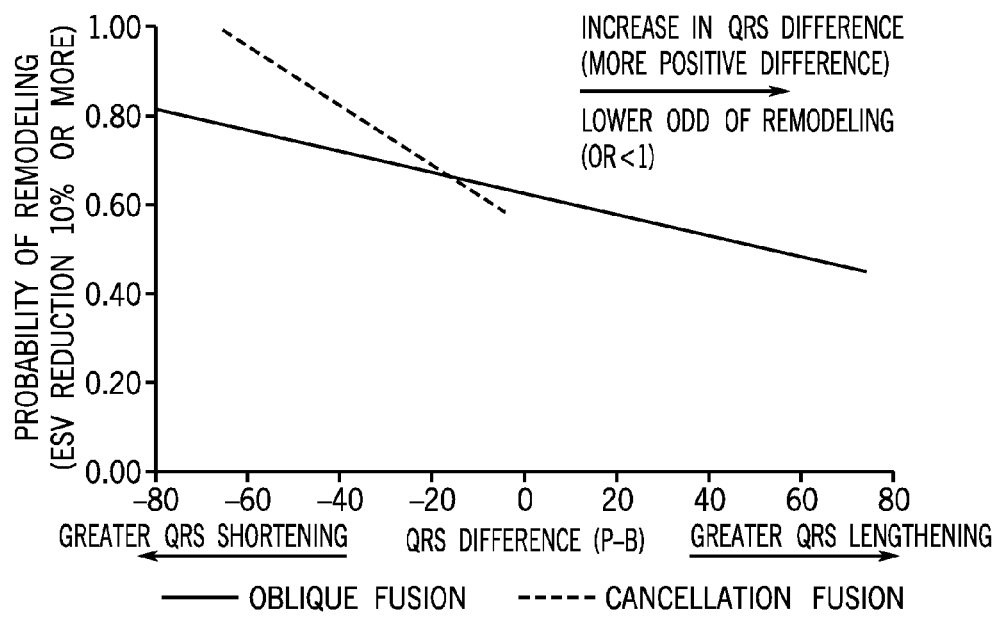

SYSTEM AND METHOD FOR AUTOMATED ADJUSTMENT OF CARDIAC RESYNCHRONIZATION THERAPY CONTROL PARAMETERS

CROSS-REFERENCE TO RELATED APPLICATIONS

This application represents the national stage entry of PCT International Application No. PCT/US2012/046907 filed Jul. 16, 2012, which, claims the benefit of, U.S. Provisional Patent Application No. 61/507,760 filed Jul. 14, 2011, the disclosure of which is hereby incorporated by reference in its entirety for all purposes.

BACKGROUND OF THE INVENTION

The field of the invention is systems and methods for cardiac rhythm and heart failure management. More particularly, the invention relates to systems and methods for performing cardiac resynchronization therapy in which adjustments to pacing control parameters are automatically made in relation to a model of cardiac electrical activity, such as a model of global cardiac electrical activity.

Electrical therapies are targeted toward patients who have heart failure associated with cardiac timing abnormalities. This is due to optimal cardiac pump function depending on a condition of methodical arrangement of component parts that is precisely and dynamically orchestrated by electrical timing. This electromechanical ordering occurs at multiple anatomic levels, including within atria, between atria and ventricles, between ventricles, and especially within the left ventricle. Improper electrical timing disrupts these systematic arrangements, can occur in isolation or in various combinations at any anatomic level, and degrades cardiac pump function.

Conduction delay within the left ventricle, caused by left bundle branch block ("LBBB") and often accompanied by an atrioventricular delay, defines asynchronous heart failure. More specifically, left ventricular conduction delay due to bundle branch block causes regional heterogeneity in contraction and stretch, or asynchrony, which reduces pump function and stimulates negative left ventricular remodeling, characterized by increased chamber volumes. Experimental models have demonstrated a direct linkage between left ventricular electrical activation, cardiac mechanics, and remodeling. The conceptual basis of multisite pacing, which is also referred to as cardiac resynchronization therapy ("CRT") or biventricular pacing, for asynchronous heart failure is to minimize ventricular conduction delay, which reduces contractile asynchrony and improves chamber mechanics.

Minimization of left ventricle electrical activation asynchrony (termed "resynchronization") restores part or all of the LBBB-induced impairment in left ventricle mechanics. Resynchronization induces so-called "reverse" remodeling, characterized by ventricular volume reductions, and improved pump function, characterized by increased ventricular ejection fraction. As a result, reverse remodeling is also associated with reduced heart failure morbidity and mortality. In addition, proper adjustment of atrioventricular timing, a second order effect of CRT, maximizes left ventricle preload and diastolic filling. Accordingly, CRT can improve pump function by both unloading the asynchronous left ventricle during contraction and maximizing left ventricle preload during filling, though these two effects are independent of each other since optimal atrioventricular timing for diastolic function is not required for ventricular electromechanical resynchronization and plays no role in reverse volumetric ventricular remodeling, and reverse remodeling can occur even when the atrioventricular relationship is improperly timed or nonexistent.

The translational mechanism for resynchronization and reverse volumetric remodeling in response to multisite pacing for asynchronous heart failure is ventricular activation wavefront fusion, which is evident on a paced 12-lead surface ECG. Presence of ventricular activation wavefront fusion predicts increased probability of reverse remodeling, whereas absence of wavefront fusion predicts reduced probability of remodeling, regardless of baseline substrate conditions.

Unfavorable substrate conditions, such as high myocardial scar volume or small amounts of ventricular conduction delay, cannot be modified by pacing techniques. In contrast, pacing strategies can be readily adapted to modify ventricular activation, for example, to induce ventricular activation wavefront fusion, and such instructions can be implemented automatically in the fully ambulatory patient having a cardiac implantable electrical device ("CIED"). However, recent experimental evidence indicates that only two-thirds of CIED patients have paced surface ECG evidence of ventricular activation wavefront fusion during conventional CRT. This implies that a large inter-patient heterogeneity exists among clinical responders, and that failure to correct ventricular conduction delay, despite conventional CRT pacing, contributes significantly to volumetric remodeling nonresponse.

It would therefore be desirable to provide a system and method for cardiac resynchronization therapy that utilizes measurements correlated with improvement in clinical outcome measures, such as heart failure morbidity and mortality and, most notably, reverse volumetric remodeling. It would be further desirable to have a system and method that more accurately characterize CRT response patterns on a patient-specific basis and that result in clinically reliable measurements and changes to pacing control parameters.

SUMMARY OF THE INVENTION

The present invention overcomes the aforementioned drawbacks by providing a system and method for cardiac resynchronization therapy ("CRT") in which a model of baseline cardiac electrical activity, such as a model of global baseline cardiac electrical activity derived from various surface electrocardiograph ("ECG") signals, is utilized to automatically adjust pacing control parameters of a cardiac implantable electrical device ("CIED") are provided. More specifically, the baseline ventricular activation sequence and a paced CRT activation sequence are both characterized using an enhanced QRS complex-based visual symbol language derived from the surface ECG signals. The baseline model is compared to CRT response patterns using modified pacing control parameters in an iterative fashion based on a patient-specific fusion response pattern phenotype determination, indicative of activation sequence change, until ventricular electrical asynchrony is minimized. The pacing control parameters that result in a patient-specific optimal fusion phenotype and minimum ventricular electrical asynchrony (maximum reduction in ventricular conduction delay) are used to generate final control parameters for CRT. Thus, this method elaborates an operational framework for improving the patient-specific response during CRT using ECG fusion phenotype recognition and linked electrical resynchronization metrics to select an optimal left ventricle lead site and titrate best electrical resynchronization metrics.

It is an aspect of the invention to provide a method for delivering cardiac resynchronization therapy to a patient's heart with a cardiac rhythm management (CRM) device. The method includes acquiring signals representing cardiac electrical activity in the patient's heart using electrodes in electrical communication with the CRM device and comparing the acquired cardiac electrical activity signals with a baseline cardiac electrical activity that is derived from surface-lead electrocardiogram measurements. The method also includes determining a ventricular activation fusion response phenotype based on the comparison and setting one or more pacing control parameters based on the determined ventricular activation fusion response phenotype. Cardiac resynchronization therapy is then delivered to the patient's heart using the one or more pacing control parameters.

It is another aspect of the invention to provide a cardiac implantable electrical device for delivering cardiac resynchronization therapy to a patient's heart. The cardiac implantable electrical device can include an input for receiving signals indicative of cardiac electrical activity in the heart, an impulse delivery system for delivering electrical impulses to the heart in order to provide cardiac resynchronization therapy thereto, a memory for storing pacing control parameters and a baseline cardiac electrical activity derived from surface electrocardiograph signals, and a processor in communication with the memory. The processor is configured to receive the received signals, compare the received signals to the baseline cardiac electrical activity using a morphological framework that characterizes the received signals as surrogates for global cardiac electrical activity, and determine a ventricular activation fusion response phenotype based on the comparison. The processor is further configured to adjust the stored pacing control parameters based on the determined ventricular activation fusion response phenotype and the comparison of the received signals with the stored baseline cardiac electrical activity, and communicate with the impulse delivery system to provide cardiac resynchronization therapy to the heart in accordance with the received at least one of the determined and adjusted pacing control parameters.

It is yet another aspect of the invention to provide a system for delivering cardiac resynchronization therapy to a patient's heart with a cardiac rhythm management (CRM) device. The system includes an input configured to be coupled to electrodes in electrical communication with the CRM device to acquire signals representing cardiac electrical activity in the patient's heart and an output configured to communicate operational control parameters to the CRM device. The system also includes a processor configured to receive the signals representing cardiac electrical activity, access baseline cardiac electrical activity information, and compare the signals representing cardiac electrical activity with the baseline cardiac electrical activity. The processor is further configured to determine a patient-specific activation fusion response phenotype based on the comparison of the signals representing cardiac electrical activity with the baseline cardiac electrical activity, determine at least one adjusted operational control parameter for controlling pacing using the activation fusion response phenotype, and communicating the at least one adjusted operational control parameter to the CRM device to perform cardiac resynchronization therapy using the at least one adjusted operational control parameter.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 6 is a schematic illustration of fusion response phenotypes in relation to cardiac stimulation sites;

FIG. 7 is a graph illustrating a relationship between odds of reverse remodeling and QRS duration changes in response to stimulation when stimulation is provided at lateral and anterior stimulation sites;

FIG. 8 is a graph illustrating a relationship between odds of reverse remodeling and QRS duration changes by fusion response phenotype;

DETAILED DESCRIPTION OF THE INVENTION

Conventional cardiac pacing with implanted cardiac rhythm management ("CRM") devices, such as pacemakers and implantable cardioverter-defibrillators ("ICDs") with pacing functionality, involves delivering electrical pacing pulses to a patient's heart via intracardiac electrodes that are in electrical contact with desired portions of the heart. The CRM device is usually implanted subcutaneously on the patient's chest.

Conventional cardiac implantable electrical device ("CIED") approaches to manual, automatic, or semi-automatic adjustment of pacing control systems for cardiac resynchronization therapy ("CRT") are limited in that they rely solely on physiologically uninformed device-based measurements that have not been correlated with improvement in any clinical outcome measure, such as heart failure morbidity and mortality and, most notably, reverse volumetric remodeling. Reasons for failing to make these correlations include lack of knowledge regarding physiologic parameters that are essential to CRT response, inadequate understanding of how these parameters are related to the probability of improvement in cardiac function, and lack of knowledge regarding informed targeting of these parameters with pacing stimulation techniques. As will be described, the present invention provides the ability to avail the clinician of an improved understanding of the interaction between substrate conditions, therapy implementation and delivery, and therapy response to yield enhanced outcomes in clinical responders and transform non-responders to clinical responders.

Figure 1:
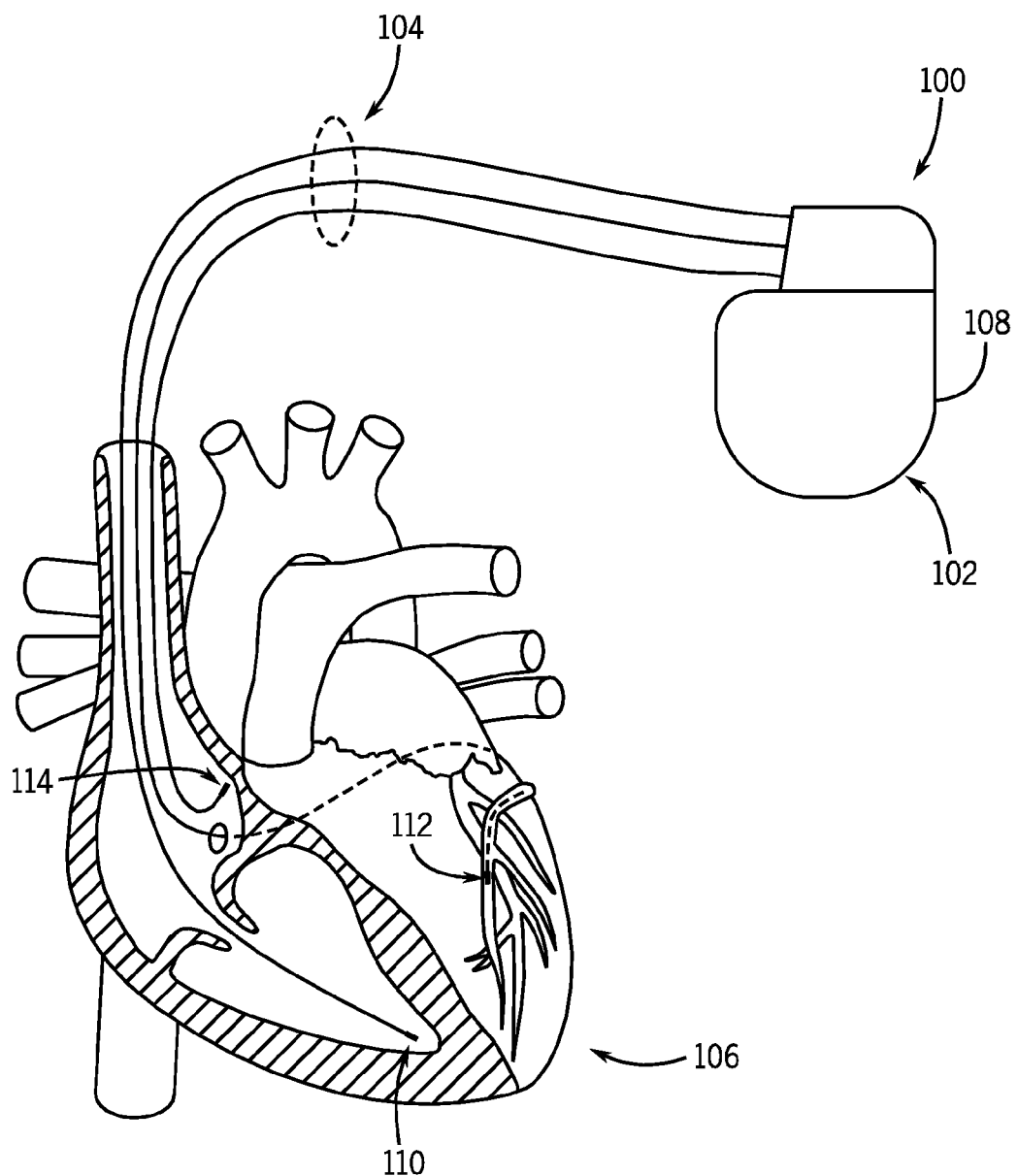
FIG. 1 is a pictorial representation of an exemplary cardiac implantable electronic device ("CIED") for cardiac rhythm management ("CRM") employed when practicing embodiments of the present invention.

Referring now to FIG. 1, an exemplary CIED 100 utilized for CRT is illustrated. Such an exemplary CIED 100 includes an implantable pulse generator 102 that is in electrical communication with an intracardiac lead system 104.

Portions of the intracardiac lead system 104 may be inserted into the patient's heart 106 by way of the vessels of the upper venous system, such as the superior vena cava; or other methods of access to the heart. The intracardiac lead system 104 includes one or more electrodes configured to produce an electrogram ("EGM") signal representing cardiac electrical activity sensed at the location of the electrode, between spatially separated electrodes, or between various combinations of electrodes and a housing 108 of the pulse generator 102, or to deliver pacing electrical pulses to the location of the electrode. Optionally, the intracardiac lead system 104 may include one or more electrodes configured to sense physiological parameters, such as cardiac chamber pressure, motion, contractility, vibration or temperature.

The lead system 104 may include one or more intracardiac electrodes 110-114 positioned in, on, or about one or more heart chambers for sensing electrical signals from the patient's heart 106 and delivering pacing pulses to the heart 106. The intracardiac electrodes 110-114, such as those illustrated in FIG. 1, may be used to sense electrical activity in or pace one or more chambers of the heart, including the left ventricle, the right ventricle, the left atrium, and the right atrium. The lead system 104 may include one or more defibrillation electrodes for delivering cardioversion/defibrillation electrical shocks to the heart.

The pulse generator 102 includes circuitry for detecting cardiac arrhythmias and controlling pacing or defibrillation therapy in the form of electrical stimulation pulses or shocks delivered to the heart 106 through the lead system 104. The housing 108 of the pulse generator 102 also serves as a sensing electrode for recording far-field EGMs in combination with various selectable intracardiac electrodes 110-114. Such a controller is formed of a microprocessor in electrical communication with a memory for program and data storage. Other controller designs will be readily appreciated by those skilled in the art.

The pulse generator 102, acting as the controller, is configured to operate the CIED 100 in a number of programmed modes, each programmed mode defining how pacing pulses are output in response to sensed cardiac electrical activity or in the absence of spontaneous cardiac electrical activity. Communications circuitry is also provided for facilitating communication between the controller and an external communication device, such as, for example, a portable or bed-side communication station, patient-carried/worn communication station, or external programmer. The communications circuitry may also facilitate unidirectional or bidirectional communication with one or more implanted, external, cutaneous or subcutaneous physiologic or non-physiologic sensors, patient-input devices, or information systems.

The controller controls the overall operation of the CIED 100 in accordance with programmed instructions stored in memory. More specifically, the sensing circuitry of the CIED 100 generates multiple atrial, ventricular, and far-field EGM signals (which indicate the time course and amplitude of cardiac depolarization that occurs during either an intrinsic or paced beat), alone and in various combinations, from the voltages sensed by the electrodes of a particular channel. The controller interprets the EGM signals sensed from the intracardiac electrodes 110-114, and far-field electrodes formed with the housing 108 of the pulse generator 102, and controls the delivery of pacing electrical pulses in accordance with a programmed pacing mode.

A morphological framework is developed to provide direct, comparative analysis of EGMs acquired with a CIED, or other CRM device, and electrocardiograms acquired with an electrocardiograph ("ECG") device employing a surface-lead system. Particularly, a model of cardiac electrical activity is formed from ECGs acquired before and after pacing with a CRM device. Thus, this model conveys information pertaining to abnormal baseline global cardiac electrical activity, changes in global cardiac electrical activity effectuated by a CRM device, and desirable global cardiac electrical activity that maximizes ventricular activation wavefront fusion, thereby guaranteeing maximum odds of improvement in cardiac pump function. While the EGMs do not share the same point-of-view as the surface-lead system commonly employed by an ECG device to record global cardiac activity, by way of the morphological framework, the model of cardiac electrical activity may be directly compared to EGMs recorded by a CIED. Therefore, multiple CIED EGMs function as morphologic surrogates for surface ECG measures of global cardiac electrical activity.

Figure 2:
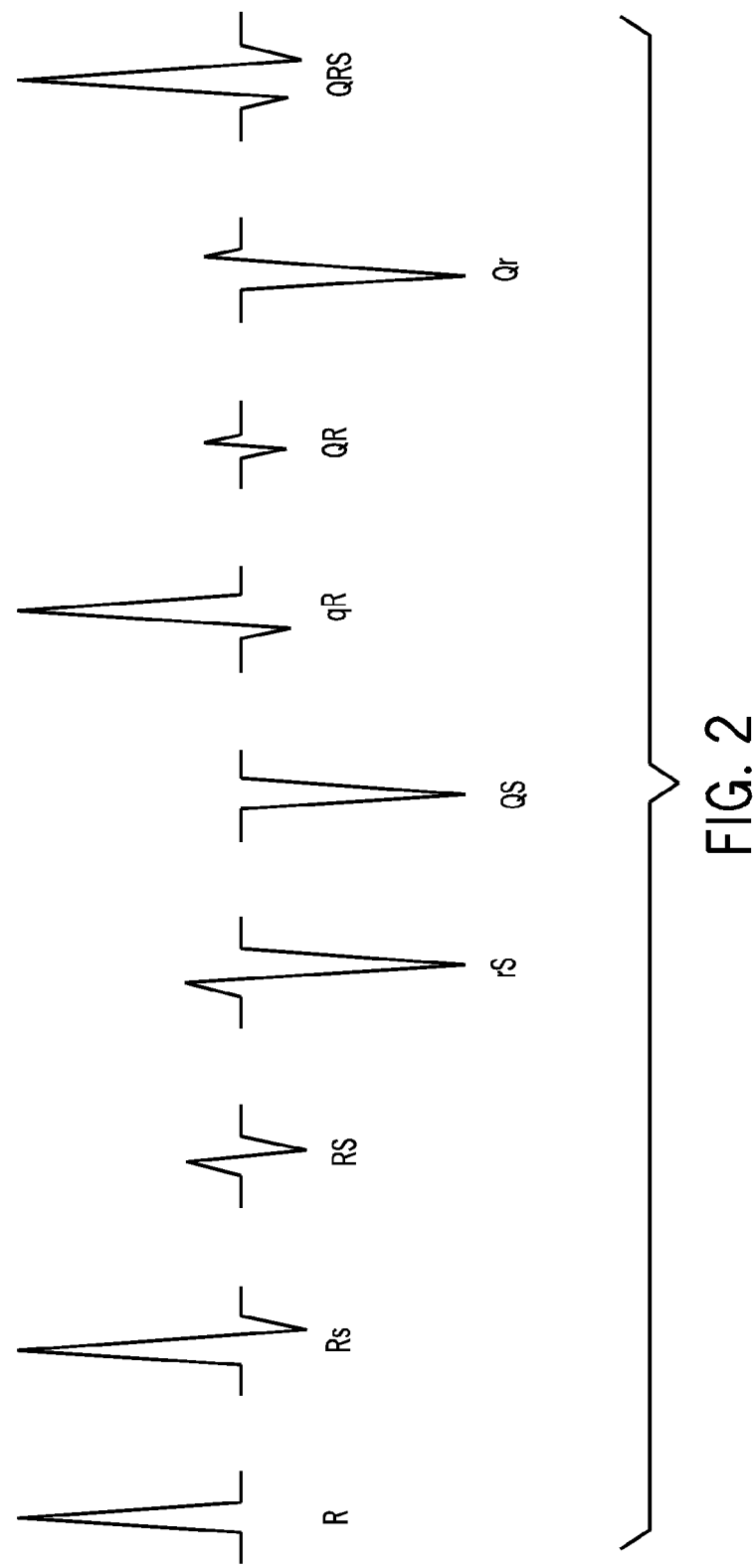
FIG. 2 is a pictorial illustration of a set of exemplary QRS complex hieroglyphs, or "glyphs," that form a morphological framework for correlating CIED measurements of cardiac electrical activity with surface ECG measurements of global cardiac electrical activity shown to predict improvement in ventricular pump function (reverse remodeling)

The morphological framework is referred to as a QRS hieroglyphic framework for ventricular activation pattern comparisons. Briefly, the pre-pacing and post-pacing QRS complex in each surface lead is deconstructed into four possible waveform elements: R, S, Q, and QS. Absolute amplitudes in millivolts ("mV") and durations in milliseconds ("ms") of all elements of each QRS complex are used to characterize specific activation patterns. Ventricular activation in each surface lead can be characterized by nine possible patterns, or QRS hieroglyphs ("glyphs"), as described below in Table 1 and illustrated in FIG. 2.

TABLE 1

| Glyph | Description |
| --- | --- |
| R | Only R-wave present |
| RS | R-wave and S-wave present with equal amplitude |
| Rs | R-wave and S-wave present, R-wave with greater amplitude |
| rS | R-wave and S-wave present, S-wave with greater amplitude |
| QS | Q-wave and S-wave present with equal amplitude |
| qR | Q-wave and R-wave present, R-wave with greater amplitude |
| QR | Q-wave and R-wave present with equal amplitude |
| Qr | Q-wave and R-wave present, Q-wave with greater amplitude |
| QRS | Q-wave, R-wave, and S-wave are all present |

The above-described glyphs are used to construct a visual symbol language for classifying a ventricular activation sequence. Each glyph characterizes a pattern of ventricular activation from a single point of view, and combinations of glyphs can be used to express activation from multiple points of view (in other words, a global perspective). Amplitude, directionality, time duration, and other aspects of component waveforms of each QRS hieroglyph can be numerically analyzed to quantify ventricular activation. For example, upon analysis, evidence for a positive change in ventricular activation (generally opposite baseline forces during ventricular conduction delay) can illustrate improvement in ventricular pump function.

Typical ventricular activation during left bundle branch block ("LBBB") is registered as right-to-left in the frontal plane, anterior-to-posterior in the horizontal plane, and variable axis on the surface ECG. By way of example for characterizing cardiac electrical activity recorded with surface leads in the QRS hieroglyph framework, this type of ventricular conduction block produces a stereotypic hieroglyphic signature with dominant positive forces in surface leads I, aVL (glyphs: R, Rs), negative forces in aVR (glyph: QS), variable forces in II, III, AVF (glyphs: R, Rs, rS, QS), dominant negative forces in V1-V2 (glyphs: QS, rS), transition in V3-V5 (glyphs: rS into Rs, R) and dominant positive forces in V5-V6 (glyphs: R, Rs). Other characteristic QRS hieroglyphic signatures can be similarly constructed for different forms of ventricular conduction block.

Experimental models of LBBB demonstrate that maximum improvement in ventricular pump function occurs when intra-left ventricle electrical asynchrony is minimized by ventricular activation wavefront fusion. Wavefront opposition and reversal during multisite pacing yields predictable ECG-evidence of ventricular activation wavefront fusion characterized by a change in directionality of QRS waveform elements expressed in two orthogonal planes, a change in amplitude (such as an emergence, increase, regression, or decrease) of QRS waveform elements, and/or a change in ventricular activation time, represented by CRT-paced QRS duration ("QRSd") relative to a baseline activation. For example, changes in frontal plane electrical axis result in normal or left axis deviation ("LADEV") changing to right axis deviation ("RADEV"). This deviation indicates reversal of activation in the frontal plane, for example, from right-to-left to left-to-right. Similarly, activation reversal in the horizontal plane is indicated by a change in dominant electrical forces from anterior-to-posterior to posterior-to-anterior. Such representative directional changes in global ventricular electrical activation are correlated, but may be manifest in differing degrees depending upon interactions between baseline electrical activation, paced activation, pacing control parameters, pacing lead position, and other considerations. An alternate way of characterizing evidence of ventricular fusion is to use regional or global measures of changes in maximum R-wave, S-wave, or QS-wave amplitude in the expected direction indicating activation wavefront reversal before and after pacing.

In addition, changes in QRS hieroglyphic signatures become apparent as rightward forces emerge in leads with dominant leftward forces. For example, qR, QR, and QS glyphs replace R, Rs, or RS glyphs in leads I and aVL. These changes indicate reversal of activation in the frontal plane (from right-to-left to left-to-right). Additionally, anterior forces emerge in leads with dominant posterior forces, as characterized by the change of the QS glyph in lead V1 to the rS, RS, Rs, or R glyph; the change of the QS or rS glyph in lead V2 to the RS, Rs, or R glyph; the change of the rS or RS glyph in lead V3 to the Rs or R glyph; and so on. These changes indicate reversal of activation in the horizontal plane (from anterior-to-posterior to posterior-to-anterior). The foregoing information pertaining to baseline surface lead measurements of global cardiac electrical activity and expected changes in those measurements during multisite pacing, translated into the QRS hieroglyph framework, is incorporated into a model of cardiac electrical activity that can be interpreted by a CIED and compared to EGMs recorded therewith.

It is noted that the expected changes in local and regional QRS hieroglyphic signatures are most pronounced in specific surface ECG leads: I, aVL, and especially V1, and V2, which are hereby designated as "pivotal leads." These pivotal leads characterize global ventricular activation in the perpendicular frontal and horizontal planes. Leads I and aVL indicate global activation in the right-to-left direction in the frontal plane, while leads V1 and V2 indicate global activation in the anterior-to-posterior direction in the horizontal plane. Therefore, an alternate approach to analysis of global ventricular activation utilizes a cardiac electrical activity model with information from a reduced surface ECG lead set (including only pivotal leads) without compromising accuracy. Accordingly, an exemplary reduced lead set includes one to two leads for evaluating activation wavefront reversal in the frontal plane (such as I, aVL leads) and one to two leads in the horizontal plane (such as V1, V2 leads). Additionally, an even more simple surface ECG lead set including only pivotal leads I and V1 could alternatively provide sufficient observational power for detecting activation wavefront reversal in the frontal and horizontal planes.

A current method for cardiac resynchronization therapy delivery is broadly summarized in two stages. First, a model of cardiac electrical activity is produced and provided to a CRM device and, second, EGMs recorded by the CRM device are compared with the provided model in real-time so that pacing control parameters are continuously adjusted to provide substantially optimal global ventricular activation wavefront fusion on a continuous, beat-to-beat, or nearly continuous basis. The model of cardiac electrical activity is produced by first acquiring ECG signals from surface leads before and after pacing. These signals are then analyzed for global ventricular activation. Using the QRS hieroglyph framework, markers of global ventricular activation wavefront fusion in the acquired ECG signals are transferred to CIED EGM surrogates for the surface ECG measurements. Such surrogates are formed of single or multiple, complementary intracardiac, local and far-field EGM QRS glyphs. These surrogates eliminate subsequent absolute reliance on a surface ECG, or alternately coexist with periodic surface ECG-based assessments and adjustments, and are the endpoint targets for automatic titration of pacing therapies on a patient-specific basis.

In the above current method, a single generic process for titration of pacing therapies is executed. However, analysis has shown that patients exhibit different responses to the general pacing therapy methods for optimizing wavefront fusion, despite continuous adjustments to pacing parameters. More specifically, ECG-based analysis of ventricular activation sequence characteristics before and after CRT in asynchronous heart failure patients illustrates three distinct, mutually exclusive and encompassing ventricular activation response pattern phenotypes to CRT. Furthermore, a patient's probability of reverse remodeling and improvement in cardiac function may be directly related to the elicited response pattern phenotype. In light of this, methods of the present invention may be used to further understand and characterize response patterns to pacing therapies and use the response patterns to determine a probability of improvement in cardiac function and maximize titration of the pacing therapies through achievement and maintenance of patient-specific evidence for optimal ventricular activation wavefront fusion based on the response patterns, therefore maximizing odds of improvement in cardiac function Generally, CRT involves advancing wavefronts from two or more sources or stimulation sites (such as the right ventricle and the most electrically delayed segment of the left ventricle during biventricular pacing). According to principles of wave mechanics, these wavefront sources may be characterized by high coherence as they are temporally and spatially constant. More specifically, because the wavefronts are initiated by stable, timed pacing stimuli through the CIED controller, they have the same frequency (in number of waves per unit time) that is, for example, equal to a constant stimulation rate. Similarly, because the stimulation sites and propagation paths are anatomically fixed, the activation wavefronts are spatially constant. It is noted that these relationships apply for any pair of stimulating electrodes (for example, between single electrode stimulating leads, between a plurality of stimulating electrodes on a single lead, or between leads with multiple electrodes).

A fusion wavefront is a composition of the individual wavefronts and is influenced by the phase relationship and amplitudes of the individual wavefronts. Phase relationship is influenced by stimulation timing (such as simultaneous vs. sequential stimulation), path length, and barriers to wavefront propagation (such as scar volume). Generally, a consequence of high wavefront coherence is that the relative phase relationship between wavefronts is constant, or fixed. However, it is possible that some dynamic variation in wavefront behavior could occur due to fluctuation in conduction properties of the intervening myocardial tissue. Furthermore, the wavefront phase relationship can be altered by manipulation of pacing control parameters. As such, the collective fusion wavefront can be manipulated by pacing control parameters to achieve specific, desired patterns correlated with increased odds of clinical improvement (specifically, reverse remodeling) and tailored to the individual patient.

According to the present invention, a conceptual framework using wave mechanics is provided to analyze wavefront propagation for general recognition of effective or ineffective ventricular activation wavefront fusion response. More specifically, this framework provides a theoretical construct for characterizing specific activation patterns during LBBB and CRT. In this construct, CRT illustrates an example of high coherence wavefront interference between individual advancing wavefronts from two or more sources or stimulation sites (such as the right ventricle and the most electrically delayed segment of the left ventricle during biventricular pacing). Taking this a step further than a simple effective/ineffective observation, exhibited wavefront interference characteristics can be differentiated into three distinct, mutually exclusive and encompassing ventricular activation response pattern phenotypes to CRT (an oblique fusion responder phenotype, a cancellation fusion responder phenotype, and a summation fusion non-responder phenotype), as further described below.

As described above, a fusion wavefront is a composition of individual wavefronts and is influenced by the phase relationship and amplitudes of the individual wavefronts. If the propagating wavefronts are opposed, the resulting activation pattern of the fusion wavefront reflects a destructive interference. In this usage, destructive interference means that two advancing opposing wavefronts tend to cancel one another out, to varying degrees, by subtraction. Thus, in this case, a baseline ventricular activation sequence signature of LBBB will be replaced by an effective paced ventricular activation sequence of admixtures of the variably opposed advancing wavefronts. In this usage, effective means an activation sequence that reduces ventricular conduction delay relative to LBBB, a necessary requirement for improvement in left ventricle ("LV") pump function.

In contrast, the observation of an exaggeration of the LBBB baseline activation sequence during CRT is characterized by constructive interference. In this usage, constructive interference means that the two advancing wavefronts enhance one another by summation, and therefore worsen the baseline ventricular conduction defect. This form of ineffective paced ventricular activation sequence, or fusion failure, does not reduce ventricular conduction delay relative to LBBB, thereby eliminating the possibility of an improvement in LV pump function. Also, in some cases, constructive interference may enhance the underlying ventricular conduction delay.

The above-described interference patterns can be characterized by analyzing relative phase relationship (relative timing of wavefront peaks and troughs) and relative wave amplitudes of propagating wavefronts in comparison to a baseline wavefront sequence. In addition, a difference calculation between the QRS durations ("QRSd") of the paced waveform and the baseline waveform can reflect the phase relationship and relative amplitudes of the waveforms, as well as quantify the change in total ventricular electrical asynchrony. This difference calculation, termed "QRSdiff" (or alternatively, "QRSdec"), can be derived from a 12 lead ECG according to the formula:

$$QRSdiff=(pQRSd)(bQRSd)$$

Baseline QRSd ("bQRSd") is a measure of total baseline ventricular electrical activation time ("bVAT"). Paced QRSd ("pQRSd") is a measure of total paced ventricular activation time ("pVAT"). Therefore, QRSdiff is a measure of the difference in total ventricular activation ("VAT") before and after CRT. When the pQRSd is shorter than the bQRSd, the QRSdiff is negative (less than zero), indicating a reduction in total ventricular electrical asynchrony and more efficient electrical resynchronization. An increasingly negative QRSdiff indicates a greater correction of the baseline ventricular conduction delay and is associated with increased odds of reverse remodeling, relative to a less negative QRSdiff value. In contrast, when the pQRSd is longer than the bQRSd, the QRSdiff is positive (greater than zero), indicating an increase in total ventricular electrical asynchrony and less efficient electrical resynchronization, which may be correlated with reduced odds of reverse remodeling (in combination with additional evidence, such as absence of a positive change in ventricular activation sequence, as further described below). In addition, accordingly, a neutral, or zero value QRSdiff indicates no change in VAT. QRSdiff may also be used as a change measure for baseline LV conduction delay in response to CRT. QRSdiff accounts for baseline LV conduction delay, for example in terms of maximum left ventricle electrical activation time ("LVATmax"). For any given pQRSd, a larger (more negative) QRSdiff implies that LVATmax has been reduced (from a longer bQRSd). Conversely, a smaller (more positive) QRSdiff implies that LVATmax is unchanged or prolonged.

In relation to the above-described wavefront interference patterns and characteristics, three distinct, mutually exclusive observed wavefront fusion phenotypes are described in the following paragraphs. Identification of these phenotypes can assist in determining the probability of reverse remodeling and can also be used to provide specific titration sequences for determining pacing parameters for optimal CRT.

Oblique (asymmetric) fusion responder phenotype

An oblique or asymmetric fusion wavefront illustrates a combination of indirectly opposing wavefronts. In this usage, the term "oblique" refers to wavefront interference that is neither parallel nor perpendicular. The individual wavefronts are characterized by high coherence (identical frequency), a constant but moderately inverse phase relation (greater than −90 degrees, but less than −180 degrees), and equivalent or differing peak amplitudes.

The destructive wavefront interference of an oblique or asymmetric fusion wavefront phenotype is characterized by emergence of new QRS component waveforms and regression of preexisting component waveforms in the expected directions of conduction delay reversal, indicating an effective or positive change in activation sequence (in comparison to a baseline wavefront measured prior to CRT). A negative QRSdiff (showing a reduction in total ventricular electrical asynchrony) is not required to characterize this phenotype, but is often observed, and is influenced by pacing control parameters. In some patients, QRSdiff is neutral or reduced (more positive) despite a positive change of activation sequence in the expected direction. In addition, the oblique fusion responder phenotype is most often observed with lateral wall stimulation sites.

Figure 3A:
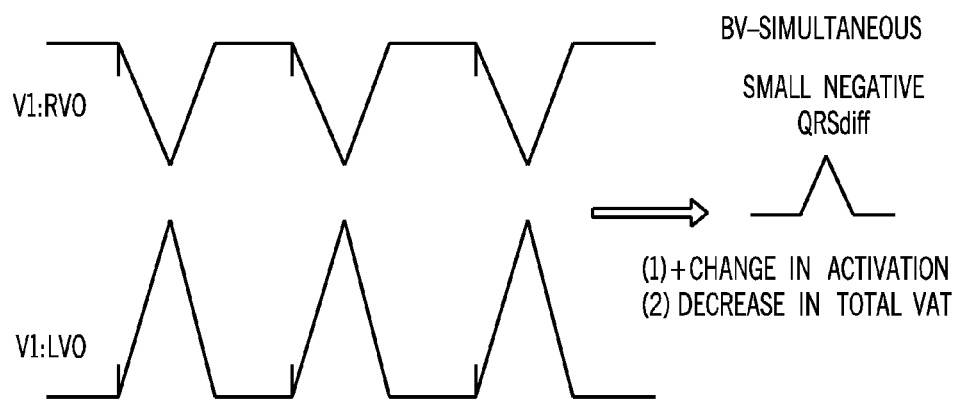
FIGS. 3A-3F are pictorial illustrations of stimulation wavefronts and resulting fusion wavefronts indicative of an oblique fusion response phenotype.

Schematic representations of various example wavefronts characteristic of the oblique fusion wavefront phenotype are shown in FIGS. 3A-3F. Specifically, FIG. 3A illustrates a monochamber right ventricle wavefront output ("RVO") and a monochamber left ventricle wavefront output ("LVO") during simultaneous biventricular pacing from a lateral stimulation site. The two wavefronts illustrate high coherence, unequal amplitudes (LVO greater than RVO), temporal alignment, and an anti-phase relationship. The resulting fusion wavefront illustrates an R glyph indicating a positive change in activation, and a slightly negative QRSdiff indicating a slight decrease in total VAT. Methods for determining these characteristics in comparison to baseline wavefronts are further described below.

Figure 3B:
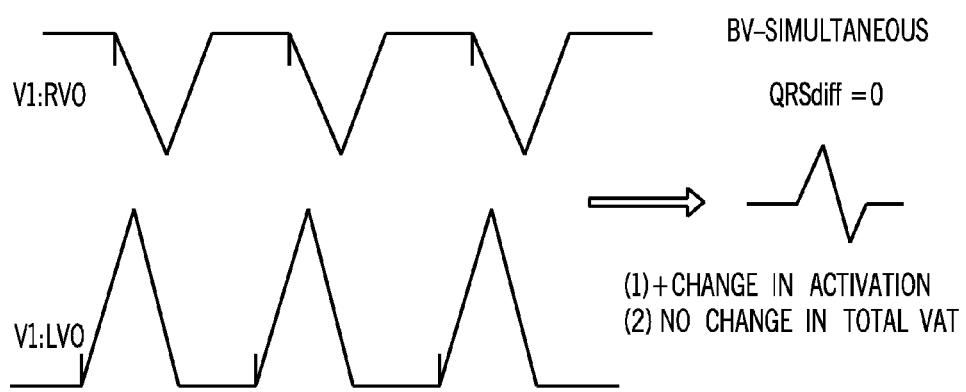

FIG. 3B illustrates an RVO wavefront and an LVO wavefront during simultaneous biventricular pacing from a lateral stimulation site. The two wavefronts illustrate high coherence, unequal amplitudes (LVO greater than RVO), temporal misalignment (due to different conduction times or conduction paths), and a moderately out of phase relationship. The resulting fusion wavefront illustrates a RS glyph indicating a positive change in activation, and a neutral (zero value) QRSdiff, indicating no change in total VAT.

Figure 3C:
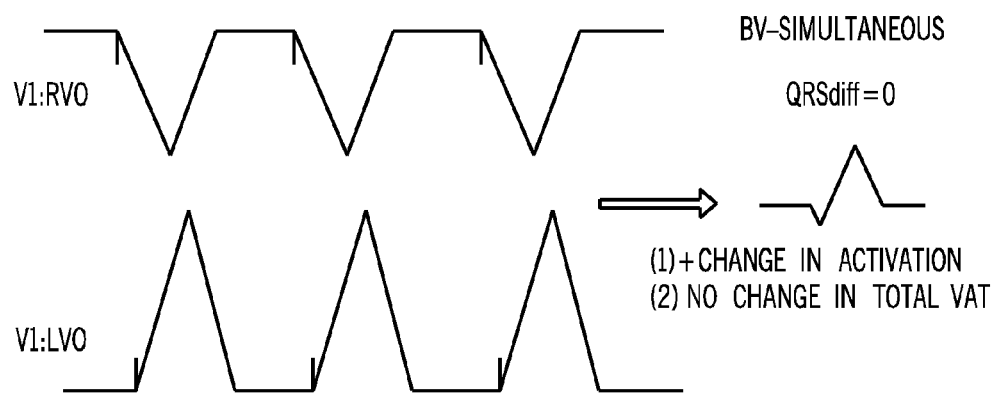

FIG. 3C illustrates an RVO wavefront and an LVO wavefront during simultaneous biventricular pacing from a lateral stimulation site. The two wavefronts illustrate high coherence, unequal amplitudes (LVO greater than RVO), temporal misalignment (due to different conduction times, with a left ventricle delay), and a moderately out of phase relationship. The resulting fusion wavefront illustrates a qR glyph indicating a positive change in activation, and a neutral (zero value) QRSdiff indicating no change in total VAT.

Figure 3D:
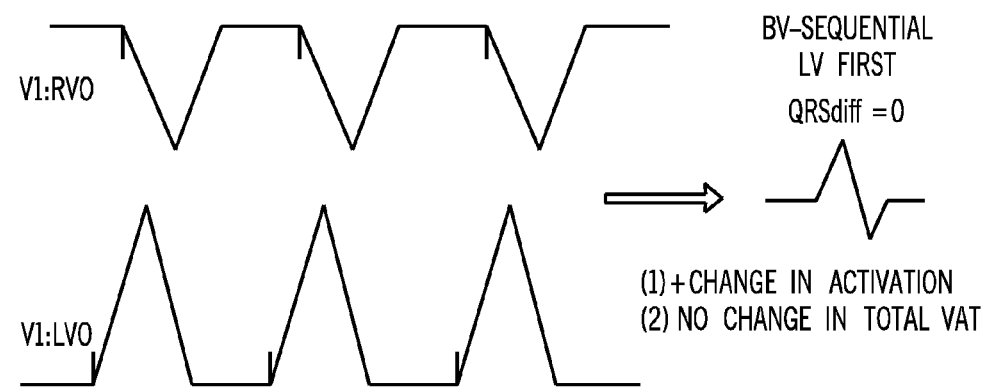

FIG. 3D illustrates an RVO wavefront and an LVO wavefront during sequential biventricular pacing (left ventricle, then right ventricle). The two wavefronts illustrate high coherence, unequal amplitudes (LVO greater than RVO), temporal misalignment (due to sequential pacing), and a moderately out of phase relationship. The resulting fusion wavefront illustrates an RS glyph indicating a positive change in activation and a neutral (zero value) QRSdiff indicating no change in total VAT.

Figure 3E:
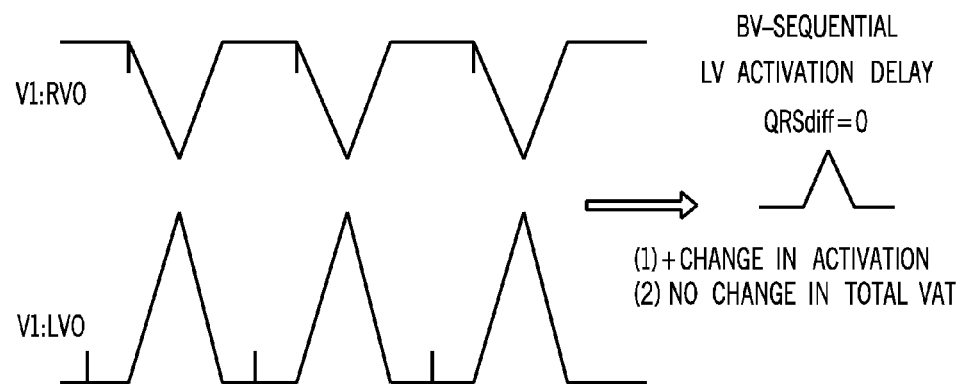

FIG. 3E illustrates an RVO wavefront and an LVO wavefront during sequential biventricular pacing (left ventricle activation delay). The two wavefronts illustrate high coherence, unequal amplitudes (LVO greater than RVO), temporal alignment (due to left ventricle capture latency or exit block), and an anti-phase relationship. The resulting fusion wavefront illustrates an R glyph indicating a positive change in activation and a neutral (zero value) QRSdiff indicating no change in total VAT.

Figure 3F:
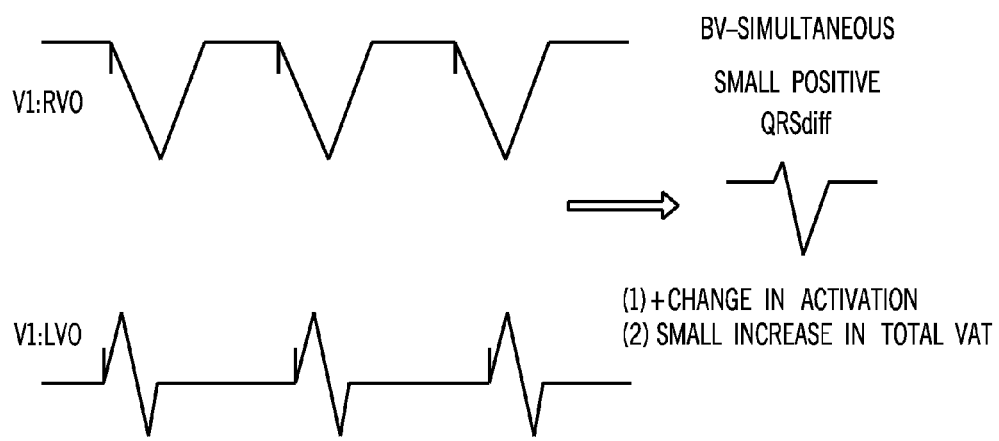

FIG. 3F illustrates an RVO wavefront and an LVO wavefront during simultaneous biventricular pacing from an anterior vein stimulation site. The two wavefronts illustrate high coherence, unequal amplitudes (RVO greater than LVO), temporal alignment, and a moderately out of phase relationship. The resulting fusion wavefront illustrates an rS glyph indicating a small positive change in activation and a slightly positive QRSdiff indicating a small increase in total VAT.

Cancellation (symmetric) fusion responder phenotype

A cancellation or symmetric fusion wavefront phenotype illustrates a combination of directly opposing wavefronts. In this usage, "cancellation" refers to wavefront interference that is directly opposed (in other words, parallel or completely out of phase). These activation wavefronts are characterized by high coherence (identical frequency), constant high inverse phase relation (approaching −180 degrees, or anti-phase), and equivalent or similar wavefront peak amplitudes.

Cancellation or symmetric fusion wavefront demonstrates a large degree of cancellation. More specifically, in such cases, where propagating wavefronts are completely out of phase, one wavefront's crests will coincide with the other wavefront's troughs and cancel out. Thus, the merged fusion wavefront is a composite reduction of both independent wavefronts due to subtraction. The destructive wavefront interference of a cancellation or symmetric fusion wavefront is characterized by extinguishing of dominant QRS component waveforms, indicating an abrupt positive change in activation sequence. All QRS waveform components are reduced and QRSdiff is maximized (indicating a large reduction in total ventricular electrical asynchrony relative to the baseline LBBB).

The cancellation fusion responder phenotype is almost exclusively observed with lateral wall stimulation sites. The paced QRSd is typically shortest with cancellation fusion responders, and as a result, QRSdiff is typically larger (more negative) for any baseline QRSd in comparison to QRSdiffs observed for the above-described oblique fusion wavefront phenotype. A large increase in QRSdiff, indicating a reduction in total ventricular electrical asynchrony, is mandatory and may be the only marker for the cancellation fusion phenotype. Furthermore, waveform regression, though typically observed, is not mandatory. For example, regression of minor (subdominant) and major (dominant) QRS waveform components in pivotal leads is typical (such as R regression in V1-V3 and QS/S regression in V1-V3), but is not required.

Figure 4:
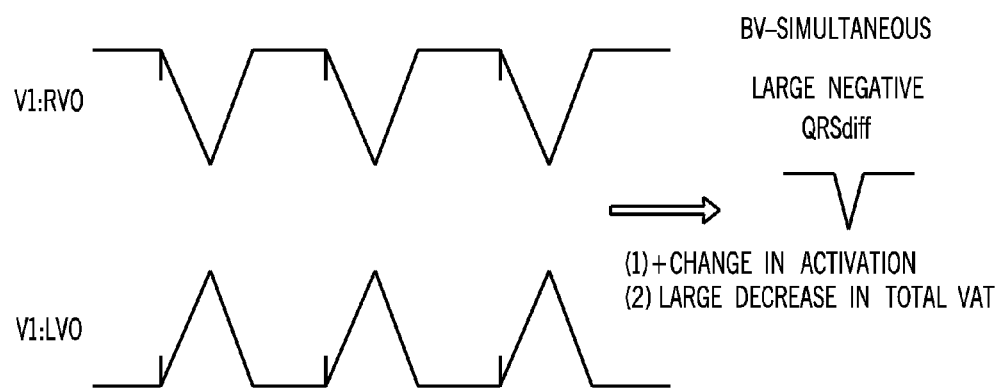
FIG. 4 is a pictorial illustration of stimulation wavefronts and a resulting fusion wavefront indicative of a cancellation fusion response phenotype.

A schematic representation of an example cancellation (symmetric) fusion phenotype is shown in FIG. 4. Specifically, FIG. 4 illustrates an RVO wavefront and an LVO wavefront during simultaneous biventricular pacing from a lateral stimulation site. The two wavefronts illustrate high coherence, equal amplitudes, temporal alignment, and an anti-phase (180-degree) relationship. The resulting fusion wavefront illustrates a qs glyph indicating a positive change in activation (regression in posterior forces), and a large negative QRSdiff indicating a large reduction in total VAT.

Summation Fusion Non-Responder Phenotype

A summation fusion wavefront phenotype illustrates a combination of in-phase wavefronts (considered parallel and non-opposing, where peaks and troughs are aligned). These activation wavefronts are characterized by high coherence (identical frequency), but a constant highly in-phase relationship, resulting in wavefront summation. The constructive wavefront interference of summation fusion wavefront is characterized by no expected QRS changes by pivotal leads, augmentation of preexisting waveforms, and neutral or positive QRSdiff (indicating increase in total VAT). There is no evidence of positive change in activation by any measure. The consequence of these relationships is that the baseline ventricular activation sequence is either unchanged or exaggerated ("amplified").

Amplification implies that the baseline ventricular conduction delay has been made worse. This may be accompanied by a neutral (no difference) or more often, a positive value for QRSdiff, indicating an undesirable increase in total ventricular electrical asynchrony (termed "conduction delay stacking"). This response pattern is most often observed with non-lateral wall stimulation sites but is also recorded at lateral wall stimulation sites during improper application of pacing control parameters and/or as a consequence of substrate-related barriers to effective paced activation wavefront propagation.

Figure 5:
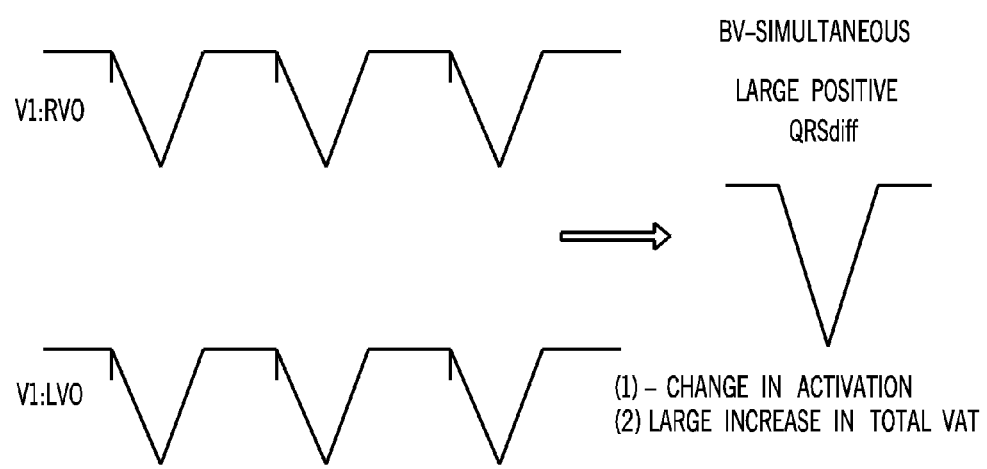
FIG. 5 is a pictorial illustration of stimulation wavefronts and a resulting fusion wavefront indicative of a summation fusion, or fusion failure, response phenotype.

The summation fusion non-responder phenotype includes two subtypes: a true, or manifest, fusion failure phenotype and a concealed fusion failure phenotype. The manifest fusion failure phenotype is illustrative of true constructive interference, as characterized above. A schematic representation of an example manifest fusion failure phenotype is shown in FIG. 5. Specifically, FIG. 5 illustrates an RVO wavefront and an LVO wavefront during simultaneous biventricular pacing from a middle cardiac vein stimulation site. The two wavefronts illustrate high coherence, equal amplitudes, temporal alignment, and an in-phase (summation) relationship. The resulting fusion wavefront illustrates a persistent QS glyph indicating no positive change in activation, and a large positive QRSdiff indicating a large increase in total VAT.

The concealed fusion failure phenotype is characterized in patients with false forms of constructive interference. That is, despite no positive change in activation sequence by any measure, a possibility exists that changes to pacing control parameters could induce a transformation to an oblique fusion or cancellation fusion response (that is, destructive interference). In particular, as further discussed below, changes to the timing of biventricular pacing (such as from simultaneous to sequential ventricular stimulation) or selection of an alternate stimulation pathway using a multielectrode LV lead, may generate sufficiently asynchronous wavefront frequency timing and reveal an oblique or cancellation fusion response phenotype that was previously concealed. A concealed fusion response may be due to differential bidirectional ventricular conduction times, usually greater from left-to-right as opposed to right-to-left, fixed conduction blocks, for example due to scar volume, functional conduction blocks, left ventricular capture latency or exit block, and/or other factors known to those skilled in the art.

FIG. 6 illustrates a summary of the relationships between pacing stimulation site, ventricular activation wavefront propagation, wavefront interference patterns, and ventricular activation response pattern phenotypes. In particular, cancellation fusion occurs during a directly opposing, or 180-degree, phase relationship between wavefronts (for example, between RV1 and LV1), oblique fusion occurs during an indirectly opposing, or 90 to 180-degree, phase relationship between wavefronts (for example, between RV1 and LV2), and summation fusion occurs during an in-phase, or 0 to 90-degree, phase relationship between wavefronts (for example, between RV1 and LV4). Interactions between these illustrated parameters in relation to reverse remodeling may be used to formulate automatic titration of CRT specific to fusion response phenotypes, as further discussed below.

Each of the above fusion response phenotypes can be generally correlated with a probability of reverse remodeling and improvement of cardiac function. Furthermore, identification of the correct fusion response phenotype, in addition to other parameters, can be used to more specifically estimate the odds of reverse remodeling. It is recognized that, while no single parameter of substrate, LV stimulation site, application of pacing control parameters, or ventricular activation fusion response pattern is sufficient to explain the odds of reverse remodeling on an individual patient basis, research indicates that highest odds of remodeling are observed in patients with combinations of favorable parameters, whereas lowest odds of remodeling occur in patients lacking multiple favorable parameters. In addition, strong representation of one or more favorable parameters can overcome absence of one or more favorable parameters. Reciprocally, in some instances, a single strongly negative parameter (such as a small left ventricle activation time) cannot be overcome by any combination of favorable parameters. For example, Table 2 below illustrates characteristic parameter combinations indicative of high, medium, and low reverse remodeling probabilities, including example overall remodeling rates, and reverse remodeling rates associated with observed oblique fusion phenotypes and cancellation fusion phenotypes under such conditions.

TABLE 2

| Remodeling probability type | | Characteristics | Overall remodeling rate | Oblique Fusion Phenotype | Cancellation Fusion Phenotype |
|---|---|---|---|---|---|
| High | ✓ | Oblique or Cancellation Fusion Phenotype | ~90% | ~80% | ~90% |
| | ✓ | Lateral lead | | | |
| | ✓ | Large QRS decrease → Large QRSdiff | | | |
| | ✓ | QRS score does not matter | | | |
| Medium | ✓ | Oblique or Cancellation Fusion Phenotype | 65% | 69% | 55% |
| | ✓ | Lateral lead | | | |
| | ✓ | Small QRS decrease or increase→ small QRSdiff or positive | | | |
| | ✓ | QRS score does not matter | | | |
| | ✓ | Oblique or Cancellation Fusion Phenotype | 60% | 70% | 56% |
| | ✓ | Non-Lateral lead | | | |
| | ✓ | Low QRS Score (scar) | | | |
| | ✓ | QRSdiff does not matter | | | |
| Low | ✓ | Oblique or Cancellation Fusion Phenotype | 26% | 27% | 25% |
| | ✓ | Non-Lateral lead | | | |
| | ✓ | High QRS Score (scar) | | | |
| | ✓ | QRSdiff does not matter | | | |

With reference to Table 2 above, it can be recognized that oblique and cancellation fusion phenotypes (illustrating destructive interference) are associated with increased odds of reverse remodeling, while manifest fusion failure phenotypes (illustrating constructive interference) are associated with substantially reduced or absent odds of reverse remodeling. Also, the effect of QRSdiff on reverse remodeling is greatest for lateral wall stimulation sites and minimal for non-lateral wall stimulation sites. That is, odds of remodeling are largely indifferent to the value of QRSdiff for non-lateral sites, as illustrated in FIG. 7. As a result, CRT pacing control parameters may be impacted by knowledge of the left ventricle stimulation site. In addition, the effect of QRSdiff on the odds of reverse remodeling varies by fusion response phenotype. As shown in FIG. 8, the increasing relationship between reverse remodeling and greater QRSdiff is steeper for cancellation in comparison to oblique fusion. Furthermore, remodeling rates during oblique fusion display conditional sensitivity to QRSdiff. For example, oblique fusion responder phenotypes with favorable substrate conditions (such as low LV scar scores) are correlated with higher odds of remodeling, regardless of QRSdiff, while oblique fusion phenotypes with unfavorable substrate conditions (such as high LV scar scores), remodeling rates are similarly high when QRSdiff is large (more negative) but poor when QRSdiff is small (more positive). In addition, remodeling rates during cancellation fusion are highly sensitive to QRSdiff. For example, highest remodeling rates are observed for cancellation fusion with large (more negative) QRSdiff regardless of substrate conditions, whereas substantially lower remodeling rates are observed for cancellation fusion at small, neutral or increasing QRSdiff.

Accordingly, left ventricular reverse remodeling can be viewed as the predictable result of a patient-specific three-step event chain. A first step, or "substrate step", is fixed and characterized by scar volume and LVATmax using the baseline ECG method, as described previously. A second step, or "procedural outcome step", indicates LV lead (lateral vs. non-lateral) at implant which generates the patient-specific ECG fusion response phenotype. A third step, or "ECG phenotype titration step", references chamber timing which modulates the ECG fusion response phenotype and the reduction in VAT indicated by QRSdiff. For example, Table 3 below illustrates remodeling rates based on the above three steps.

TABLE 3

| Substrate | Fusion Non-Responder Phenotype | ECG Fusion Phenotype + small QRSdiff | Titrate large QRSdiff |
|---|---|---|---|
| Lateral Stimulation Site | | | |
| Good | 40.0% | Oblique: 71.8% Cancellation: 100% | Oblique: 96.1% Cancellation: 100% |
| Poor | 47.6% | Oblique: 56.5% Cancellation: 52.4% | Oblique: 57.1% Cancellation: 87.5% |
| Non-Lateral Stimulation Site | | | |
| Good | 66.6% | Oblique: 71.4% Cancellation: 50.0% | Oblique: 42.8% Cancellation: 50.0% |
| Poor | 40.0% | Oblique: 31.2% Cancellation: 33.3% | Oblique: 75.0% Cancellation: n/a |

In accordance with Table 3 above, for patients with good substrate, lateral lead, and a fusion non-responder phenotype, the remodeling rate is 40%. For the same patient with a titrated ECG fusion response (for example, an immediate fusion response or a transformed fusion response from a concealed non-response), the rate increases to almost 72% for an oblique fusion phenotype and 100% for a cancellation fusion phenotype. If either fusion response phenotype is enhanced by further reducing VAT, remodeling rates reach 96.1% and 100%, respectively. These titration remodeling rates indicate that patients with favorable substrate conditions and already good remodeling odds can potentially be improved by LV lead site and titration of electrical resynchronization.

For patients with poor substrate conditions, a lateral stimulation site, and fusion non-responder phenotype, remodeling rate is low (47.6%). Generating either fusion response phenotype improves the rate slightly, and titration toward a large QRSdiff of cancellation fusion phenotype increases the rate to nearly 90%. For patients with good substrate conditions, a non-lateral LV lead site, and either oblique or cancellation fusion phenotype, remodeling rates are substantially lower compared to otherwise similar patients with lateral leads. Finally, for patients with poor substrate conditions and non-lateral leads, remodeling rates are low regardless of the fusion response phenotype.

In summary, the ECG phenotype is a patient-specific CRT output measure that provides immediate visual evidence for presence or absence of reversal of LV conduction delay and numerically quantifiable indices of electrical resynchronization efficiency. The fusion phenotype is displayed using a deconstructed QRS complex based symbol language. The three subtypes of fusion glyphs are generated using the principals of interference during wave propagation. Oblique and cancellation phenotypes express different degrees of effective wavefront fusion and are associated with increased odds of remodeling. The efficiency of electrical resynchronization is quantified by the patient-specific, fusion response phenotype-linked QRSdiff which enumerates the reduction in ventricular electrical asynchrony (VAT) and is associated with increased odds of remodeling. Conversely, the fusion non-response phenotype expresses wavefront summation (fusion failure), is accompanied by increased VAT and reduced remodeling. The ECG phenotypes, electrical resynchronization efficiency, and odds of reverse remodeling are strongly influenced by LV lead site. The two ECG fusion response phenotypes are generated more often from lateral leads whereas the fusion non-response phenotype is associated with non-lateral leads. For either fusion response phenotype, the decrease in VAT (QRSdiff), odds of remodeling, and LV volume reductions are greater for lateral in comparison non-lateral leads. The cancellation fusion response phenotype, which is accompanied by the largest QRSdiff, greatest reductions in LV volumes, and highest remodeling odds, is generated almost exclusively from lateral leads. Finally, the relationship between reduction in VAT (larger QRSdiff) and increased remodeling odds is steeper for lateral leads in comparison to non-lateral leads and for cancellation fusion response in comparison to oblique fusion response phenotypes.

In accordance with the present invention, methods for recognition of fusion responder phenotype generally include constructing a model of global cardiac electrical activity using the above-described ECG analytic architecture transferred to CIED-based EGM surrogates and analyzing wavefront characteristics for criteria indicative of a specific fusion phenotype.

Figure 9:
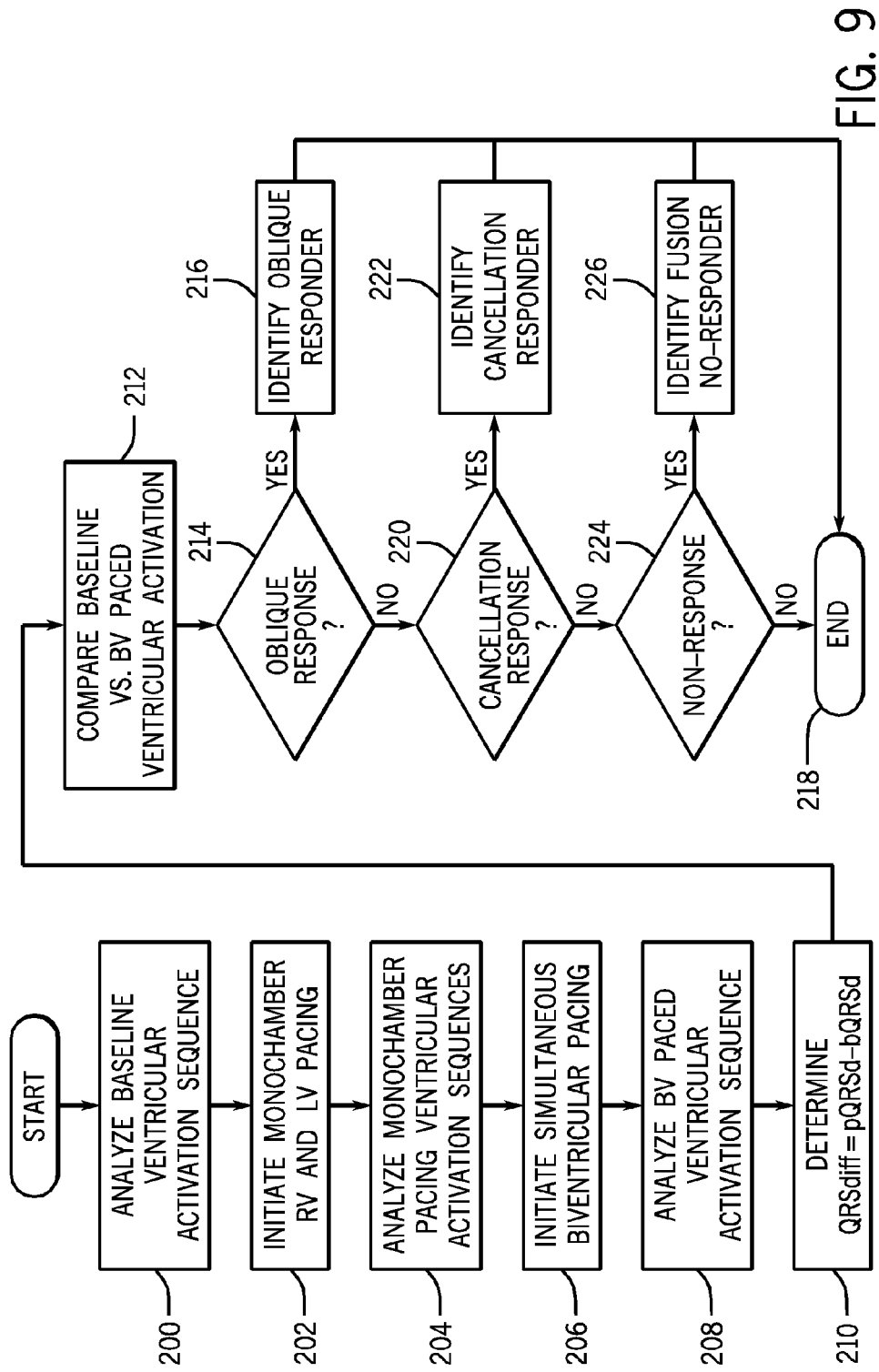
FIG. 9 is a flowchart setting forth the steps of an exemplary method for identifying a fusion response phenotype during cardiac resynchronization therapy.

More specifically, as shown in FIG. 9, a baseline ventricular activation is analyzed (process block 200) using surface ECG methodology to determine QRS hieroglyphic signatures, global measures of ventricular activation, and QRS duration. Next, monochamber right ventricle and left ventricle pacing are initiated (process block 202) and respective ventricular activation sequences are analyzed (process block 204) using surface ECG methodology to determine QRS hieroglyphic signatures, global measures of ventricular activation, and paced QRS durations. Following monochamber pacing, biventricular pacing is initiated (process block 206) and a paced ventricular activation sequence is analyzed (process block 208) using the QRS hieroglyphic methodology to determine QRS hieroglyphic signatures, global measures of ventricular activation, and paced QRS durations. During simultaneous biventricular pacing, QRSdiff is determined between the paced QRSd and baseline QRSd (process block 210). After QRSdiff is determined, the baseline ventricular activation sequence is compared to the paced ventricular activation sequence (process block 212) and a determination is made as to whether parameters indicative of oblique (asymmetric) fusion responder phenotype are satisfied (process block 214). If so, oblique fusion responder phenotype is identified (process block 216) and the identification process is completed (process block 218). If not, a determination is made as to whether parameters indicative of cancellation (symmetric) fusion responder phenotype are satisfied (process block 220). If such parameters are satisfied, cancellation fusion responder phenotype is identified (process block 222) and the identification process is completed (process block 218). If not, a determination is made as to whether parameters indicative of fusion non-responder phenotype are satisfied (process block 224). If such parameters are satisfied, fusion non-responder phenotype is identified (process block 226) and the identification process is completed (process block 218).

The set of parameters indicative of oblique fusion responder phenotype include: emergence of new anteriorly directed forces (R waves) in pivotal leads (such as V1-V3); with/without regression of posteriorly directed forces (QS, S waves) in pivotal leads (such as V1-V3); with/without regression of leftward directed forces (R waves) in pivotal leads (such as I, aVL); with/without emergence of rightward directed forces (Q, QS) in pivotal leads (such as I, aVL); QRSdiff is negative, neutral, or positive.

The set of parameters indicative of cancellation fusion responder phenotype include: no emergence of new QRS waveform components in the expected direction of activation reversal by pivotal leads; regression of posteriorly directed forces (QS, S waves) in pivotal leads (such as V1-V3); with/without regression of anteriorly directed forces (R, r waves) in pivotal leads (such as V1-V3); with/without regression of leftward forces (R waves) or amplification of rightward forces (QS, S waves) in pivotal leads (such as I, aVL); QRSdiff value is negative.

The set of parameters indicative of fusion non-responder phenotype includes no emergence of new QRS waveform components in the expected direction of activation reversal by pivotal leads; absent or minimal regression of existing waveform components in the expected direction of activation reversal by pivotal leads; amplification of existing QRS waveform components (opposite the expected direction of activation reversal); QRSdiff value is neutral or positive.

Once the fusion response phenotype is identified (as indicated by completion of the process of FIG. 9), a process, specific to the identified phenotype, for titrating pacing control parameters to achieve optimal fusion activation is initiated. Exemplary control parameter adjustments include manipulation of the paced atrioventricular interval ("pAVI"), such as by shortening, or sequentially timed biventricular ("BV") pacing timing using a ventricle-ventricle or "V-V" timing interval, such as by stimulating the electrically delayed ventricle at fixed or variable intervals prior to the early activated ventricle. In addition, in some instances, optimization of a specific fusion response phenotype may be enhanced in some patients by the use of a multielectrode LV lead, as further described below.

Figure 10:
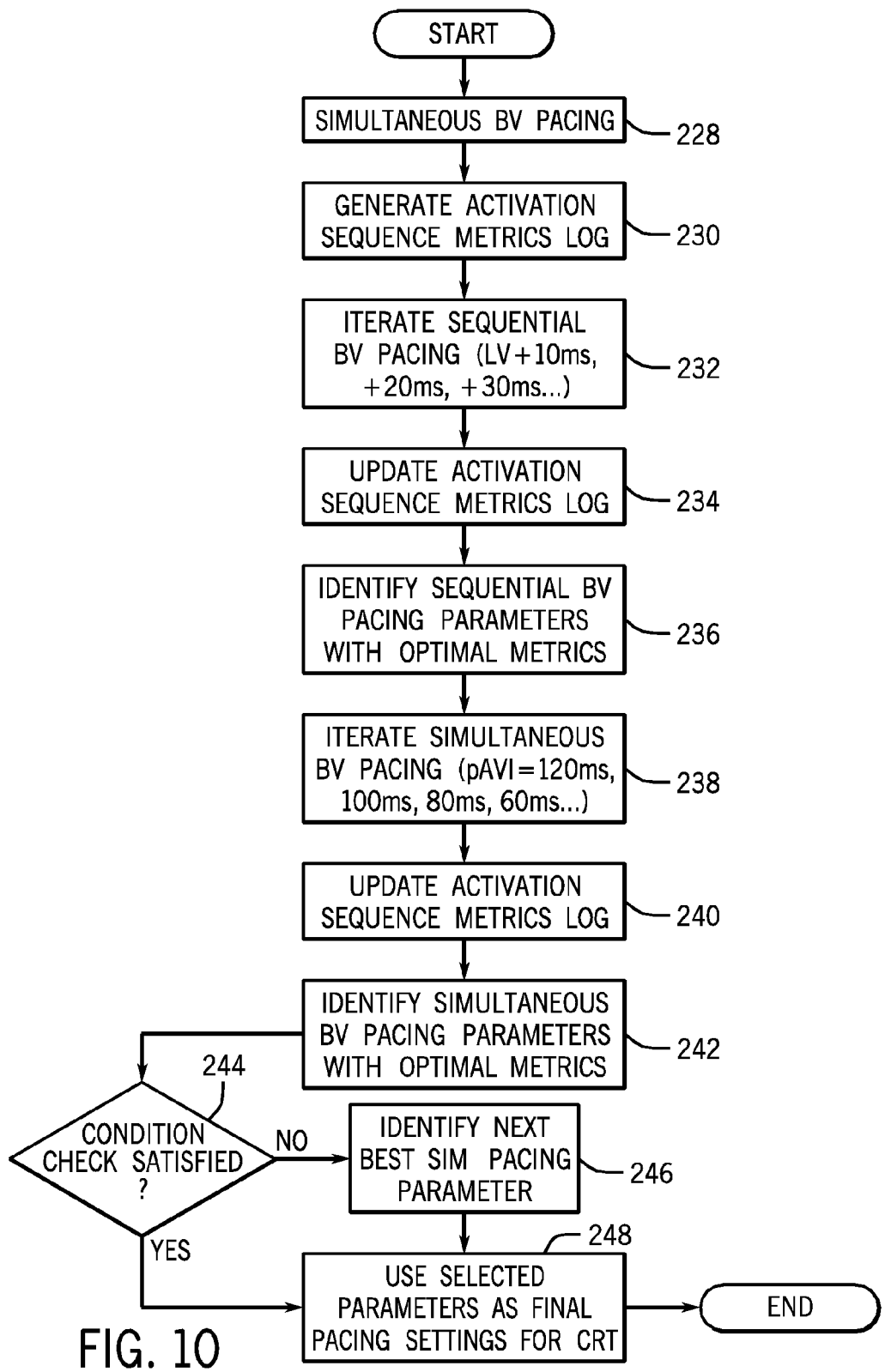
FIG. 10 is a flowchart setting forth the steps of an exemplary method for titrating cardiac resynchronization therapy pacing parameters in relation to a recognized oblique fusion response phenotype.

An overview of an exemplary process for titrating optimal activation fusion in oblique fusion responders is provided in FIG. 10. The general goal of this process is to identify a combination of pacing control settings that achieves optimal oblique fusion and atrioventricular resynchronization. Due to the relationship between the pAVI, the timing of right ventricle and left ventricle stimulation, and the correction of left ventricle conduction delay, this process may be conducted via two primary sequences: optimization of biventricular pacing (in particular, LV activation timing) and optimization of pAVI. It is understood that the process steps of FIG. 10 described below broadly summarize this approach and are not exhaustive.

Figure 11:
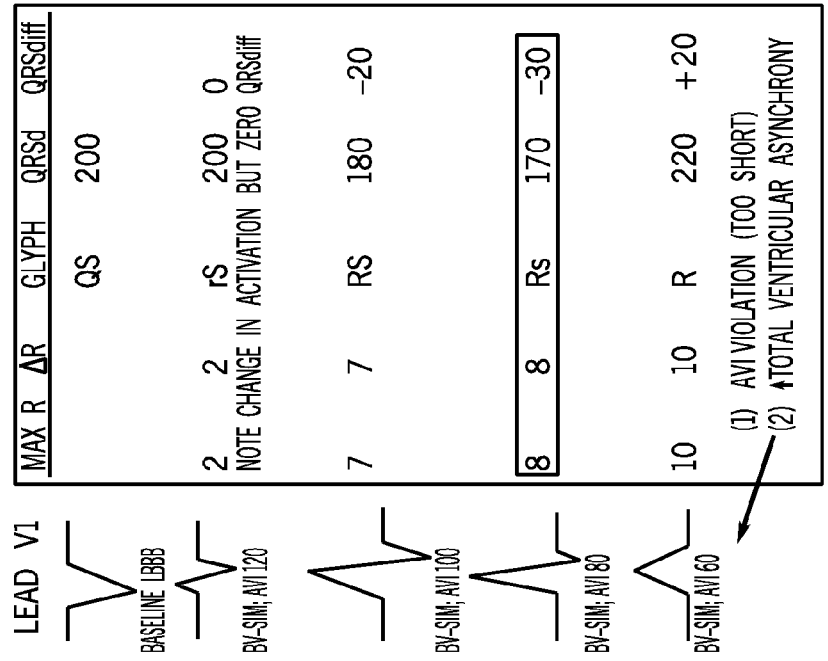
FIG. 11 is a pictorial illustration of an example activation sequence metrics log associated with the flow chart of FIG. 10.

First, simultaneous BV pacing is conducted (at process block 228), at a fixed pAVI (for example, at 100 ms, or 50% the intrinsic AVI, "iAVI"). In some instances, the simultaneous BV pacing conducted from the identification process of FIG. 9 may be continued. An activation sequence metrics log, as shown in FIG. 11, including activation sequence output metrics or measures for a baseline waveform (for example, taken before pacing) and the waveform created by the above simultaneous BV pacing, is then generated (process block 230). Such measures include, but are not necessarily limited to, maximum R wave amplitude from pivotal lead V1, change in R wave amplitude from the baseline, QRS glyph response, QRS duration and QRSdiff. The activation sequence metrics log can first include baseline metrics so that observed fusion waveform metrics may be compared visually (in terms of R wave amplitude change and QRSdiff), or numerically summarized by the processor. According to the example activation sequence metrics log of FIG. 11, the baseline waveform exhibited no R wave (and therefore a R wave amplitude of 0 mV), a QS glyph, and a QRSd of 200 ms, shown in row 1. The simultaneous BV pacing executed at process block 228 created a fusion waveform that exhibited a maximum R wave amplitude of 2 mV, a 2-mV change in R wave amplitude, an rS glyph, a QRSd of 200 ms, and a QRSdiff of 0 ms, as shown in row 2. According to this example, it may be noted that during simultaneous BV pacing, R wave emergence and S wave regression occur, as illustrated by the transformation of a QS glyph to an rS glyph, thus indicating oblique fusion.

Next, iterative sequential BV pacing is conducted (process block 232) at a fixed pAVI, such as 100 ms, where the V-V timing interval is progressively increased, that is, timing of left ventricle stimulation is progressively advanced relative to right ventricle stimulation, in incremental values (such as by +10 ms, +20 ms, +30 ms, etc.). Fusion waveform metrics at each iteration are identified and recorded in the activation sequence metrics log (process block 234). By way of example, FIG. 11 shows that sequential BV pacing with a +10-ms LV activation created a fusion waveform that exhibited a maximum R wave amplitude of 5 mV, a 5-mV change in R wave amplitude, an RS glyph, a QRSd of 180 ms, and a QRSdiff of −20 ms, as shown in row 3. Sequential BV pacing with a +20-ms LV activation created a fusion waveform that exhibited a maximum R wave amplitude of 8 mV, an 8-mV change in R wave amplitude, an Rs glyph, a QRSd of 170 ms, and a QRSdiff of −30 ms, as shown in row 4. Sequential BV pacing with a +30-ms LV activation created a fusion waveform that exhibited a maximum R wave amplitude of 10 mV, a 10-mV change in R wave amplitude, an R glyph, a QRSd of 220 ms, and a QRSdiff of +20 ms, as shown in row 5. It may be noted that, in this example, during sequential pacing, R wave amplitude progressively increases and S wave diminishes, indicating progressive reversal of the baseline conduction defect (from anterior-posterior to posterior-anterior).

The activation sequence output metrics for each sequential BV pacing setting are then surveyed (process block 236) to identify the pacing control setting, in particular, the LV activation timing, that achieves the optimal fusion phenotype wavefront, as characterized by maximum evidence of positive change in activation (as indicated by the QRS glyphs), at the minimal paced QRSd, yielding the largest negative (increased) QRSdiff. Thus, referring back to the example metrics log shown in FIG. 11, the sequential BV pacing with a +20-ms LV activation (shown in row 4) exhibited the optimal oblique fusion wavefront, as determined by a positive change in activation, minimum QRSd, and most negative QRSdiff (largest reduction in total VAT). It is noted that since oblique fusion wavefronts may exhibit a positive change in activation sequence accompanied by a neutral or decreased QRSdiff, the optimal pacing control settings under such conditions may be those which only yield the minimal paced QRSd in some instances (total VAT is neutral or increased, despite positive change in activation sequence).

Figure 12:
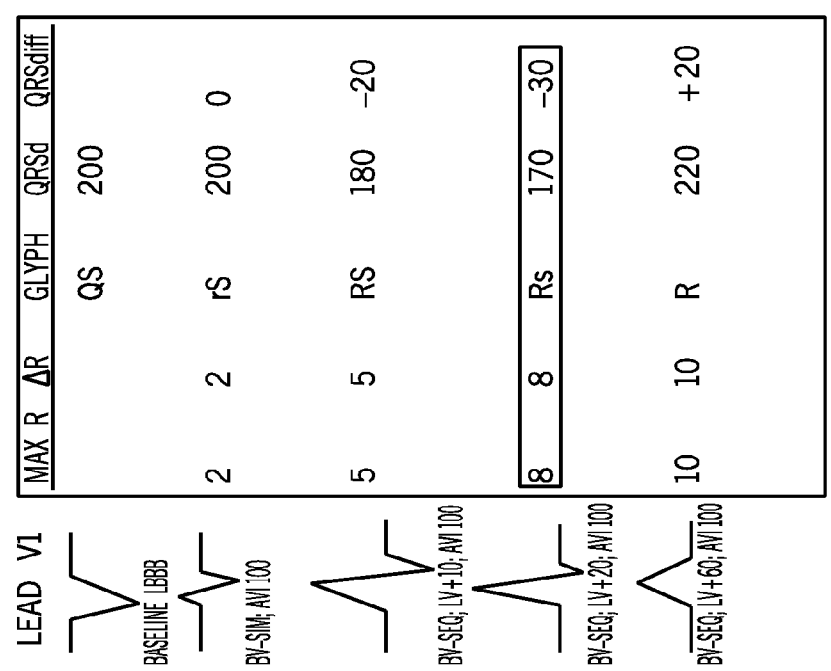
FIG. 12 is a pictorial illustration of another example activation sequence metrics log associated with the flow chart of FIG. 10.

Once the optimal LV activation timing is determined at process block 236, iterative simultaneous BV pacing is conducted (process block 238), where the pAVI is progressively changed in incremental values (such as 120 ms, 100 ms, 80 ms, 60 ms, etc.). Fusion phenotype waveform metrics at each iteration are identified and recorded (process block 240) in an activation sequence metrics log that includes at least baseline wavefront metrics. By way of example, FIG. 12 illustrates an activation sequence metrics log with a baseline waveform that exhibited no R wave (and therefore a R wave amplitude of 0 mV), a QS glyph, and a QRSd of 200 ms, as shown in row 1. Simultaneous BV pacing with a 120-ms pAVI created a fusion waveform that exhibited a maximum R wave amplitude of 2 mV, a 2-mV change in R wave amplitude, an rS glyph, a QRSd of 200 ms, and a QRSdiff of 0 ms, as shown in row 2. Simultaneous BV pacing with a 100-ms pAVI created a fusion waveform that exhibited a maximum R wave amplitude of 7 mV, a 7-mV change in R wave amplitude, an RS glyph, a QRSd of 180 ms, and a QRSdiff of −20 ms, as shown in row 3. Simultaneous BV pacing with an 80-ms pAVI created a fusion waveform that exhibited a maximum R wave amplitude of 8 mV, an 8-mV change in R wave amplitude, an Rs glyph, a QRSd of 170 ms, and a QRSdiff of −30 ms, as shown in row 4. Simultaneous BV pacing with a 60-ms pAVI created a fusion waveform that exhibited a maximum R wave amplitude of 10 mV, a 10-mV change in R wave amplitude, an R glyph, a QRSd of 220, and a QRSdiff of +20, as shown in row 5.

The activation sequence output metrics for each simultaneous pacing setting are then surveyed (process block 242) to identify the pacing control setting, in particular, pAVI, that achieves the optimal fusion wavefront, as characterized by maximum evidence of positive change in activation (as indicated by the QRS glyphs), at the minimal paced QRSd, yielding the largest negative (increased) QRSdiff. Thus, referring back to the example metrics log in FIG. 12, the simultaneous BV pacing with an 80-ms pAVI (illustrated in row 4) exhibited the optimal oblique fusion phenotype waveform, as determined by the positive change in activation, minimum QRSd, and most negative QRSdiff. As noted above, since oblique fusion wavefronts may exhibit a positive change in activation sequence accompanied by a neutral or decreased QRSdiff, the optimal pacing control settings under such conditions may be those which only yield the minimal paced QRSd in some instances.

Once the optimal pAVI setting is determined in process block 242, an additional pAVI setting check is performed (process block 244). This additional check ensures that the optimal pAVI determined at process block 242 satisfies conditions of atrial sensing and atrial pacing, as specified in prior disclosures. For example, a chosen pAVI may not satisfy such conditions if the duration is too short (such as the 60-ms pAVI from row 5 of FIG. 12). If the chosen pAVI does not satisfy such conditions, the "next best" pAVI is chosen through examination of the activation sequence output metrics (process block 246). If the pAVI does satisfy atrial sensing and atrial pacing conditions, the chosen LV activation timing and pAVI are used as final pacing control settings for CRT (process block 248). Thus, in accordance with the above method, the final pacing control settings for optimal oblique fusion may be those which satisfy the following conditions: maximize evidence of positive change in activation sequence for oblique fusion responder phenotype; minimize paced QRSd; maximize negative (increased) QRSdiff or minimal positive (decreased) QRSdiff; and satisfy optimal pAVI requirements under conditions of atrial sensing and pacing.

Figure 13A:
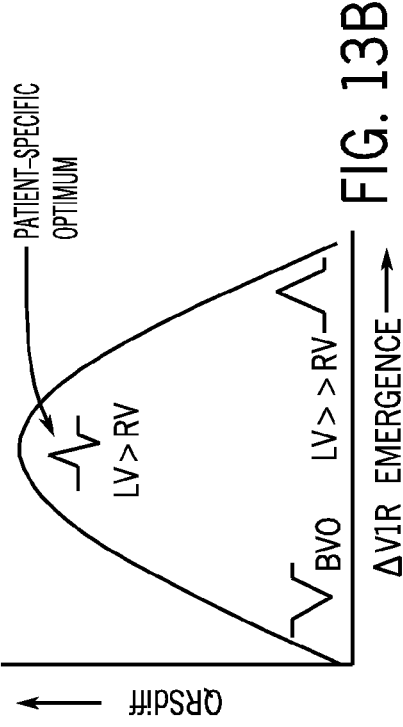
FIGS. 13A-13D are graphs illustrating patient-specific relationships of activation sequence characteristics during titration of cardiac resynchronization therapy pacing parameters.
Figure 13B:
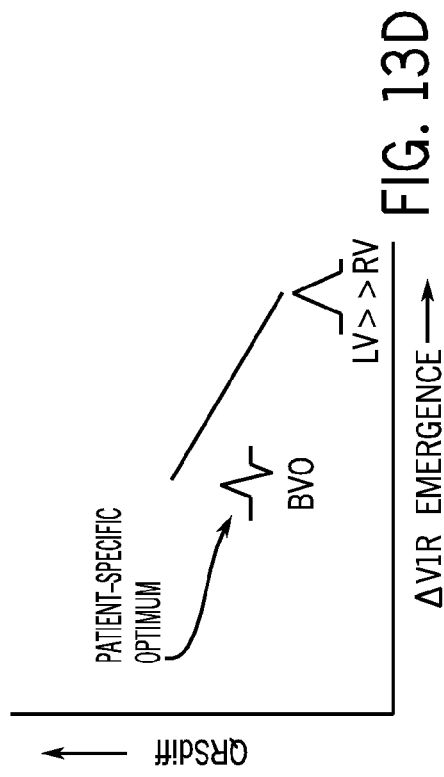
Figure 13C:
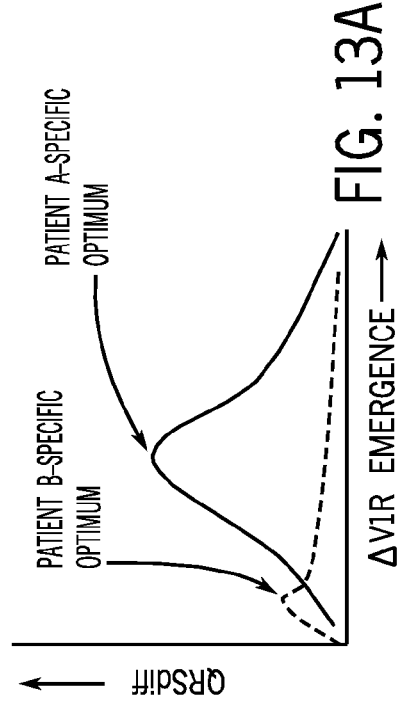
Figure 13D:
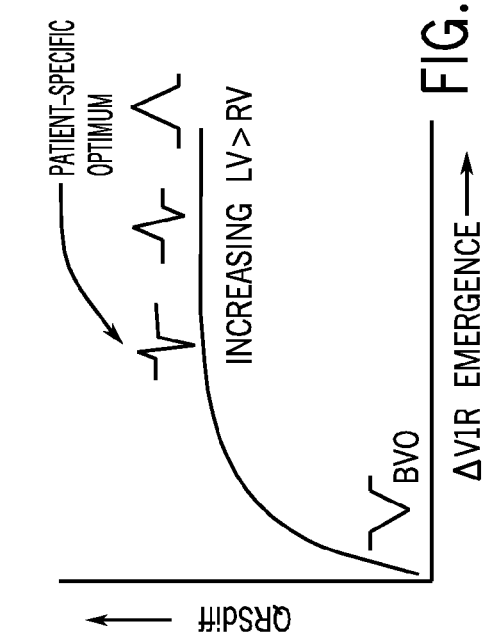

It is recognized that the change in activation sequence metrics during titration of pacing control parameters (pAVI, sequential biventricular stimulation, and/or other manipulations known to those skilled in the art) may display generally predictable trends and behaviors. For example, it is recognized to be generally true that at extremes of LV preceding RV activation, R amplitude and paced QRSd are at maximum values indicative of total activation reversal and increase in total ventricular electrical asynchrony. However, change in activation sequence metrics during titration of pacing control parameters also demonstrates substantial intra-patient and inter-patient heterogeneity. For example, FIGS. 13A-13D illustrate example patient-specific activation metrics response curves in terms of R wave emergence compared to QRSdiff. As shown in FIG. 13A, some patients display a relative "flat" oblique fusion phenotype activation metrics response curve to iterative changes in timing parameters, while others display a single pivot point of optimal oblique fusion phenotype metrics, bracketed on either side by inadequate fusion or overcorrection.

It is understood that the activation sequence metrics displayed in FIGS. 11 and 12, though accurate for determining optimal wavefront fusion, are merely representative. A multiplicity of additional metrics sufficient to permit precise quantification of changes in the QRS glyph response during the fusion titration sequence may also be collected. It is similarly understood that a parallel activation sequence change metrics log may also be constructed using similar methods and logic for the CIED glyphs that serves as quantitative surrogates for critical surface ECG glyphs. Furthermore, in some instances, the above two titration processes may be executed in parallel to further refine optimal pacing control parameters for the individual patient. An exemplary approach in this instance would iteratively vary sequential biventricular pacing across all values of permitted pAVI. This would increase the number of data points in the activation sequence change metrics log and refine the optimal pacing control parameters for the individual patient. Further, the results of these parallel titration processes may be fully integrated with optimal pAVI titration during conditions of atrial sensing and pacing.

Figure 14:
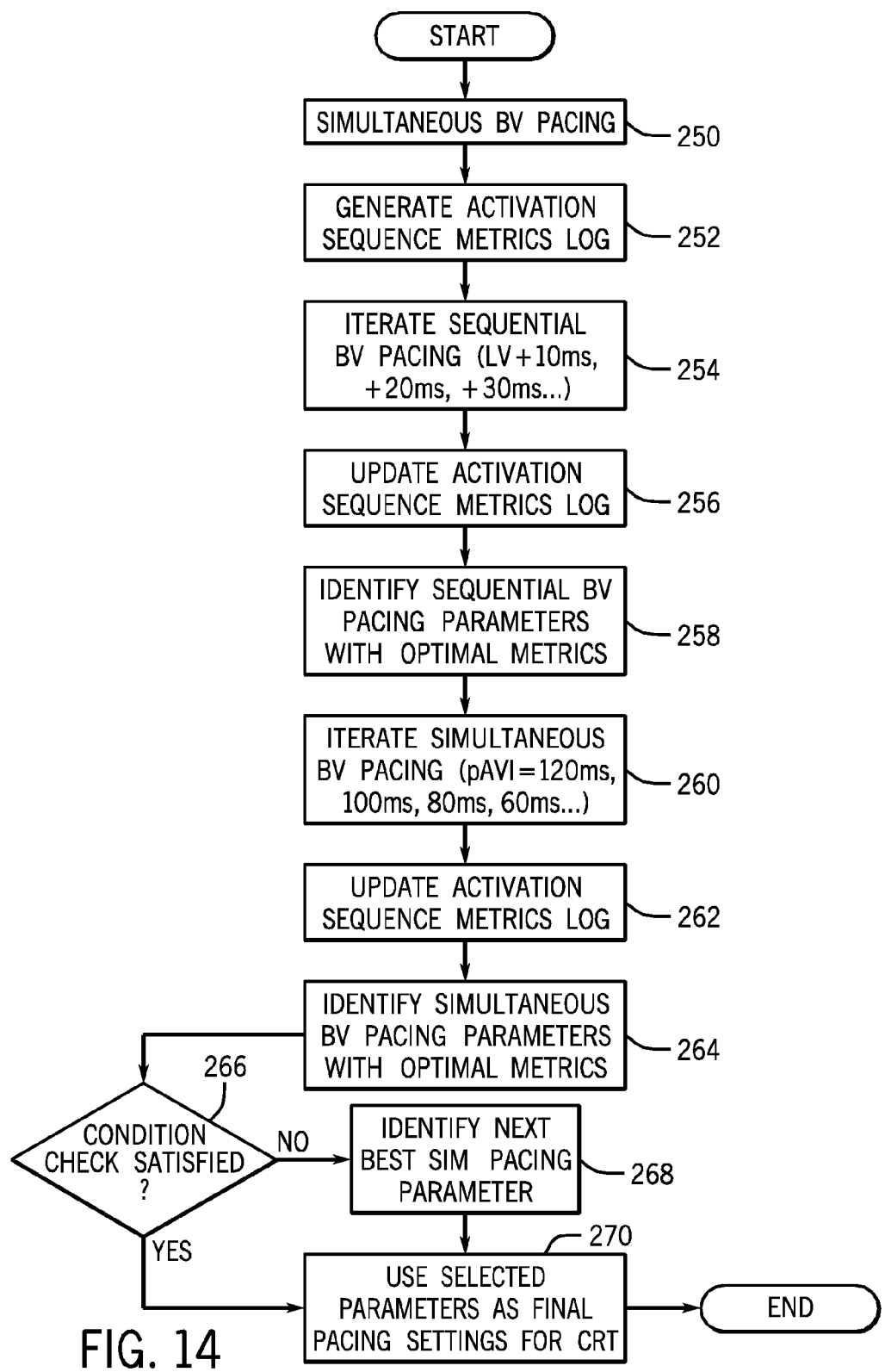
FIG. 14 is a flowchart setting forth the steps of an exemplary method for titrating cardiac resynchronization therapy pacing parameters in relation to a recognized cancellation fusion response phenotype.

An overview of an exemplary process for titrating optimal activation fusion in cancellation (symmetric) fusion responders is provided in FIG. 14. The general goal of this process is to identify a combination of pacing control settings that achieves optimal cancellation fusion and atrioventricular resynchronization. This process for optimization of cancellation fusion may be conducted with a similar logic and structure as described above with respect to oblique fusion, but can include different operating parameters and activation sequence change output metrics. In continuing with the logic described above, due to the relationship between the pAVI, the timing of right ventricle and left ventricle stimulation, and the correction of left ventricle conduction delay, this process may be conducted via two primary sequences: optimization of biventricular pacing and optimization of pAVI. It is understood that the process steps of FIG. 14 described below broadly summarize this approach and are not exhaustive.

Figure 15:
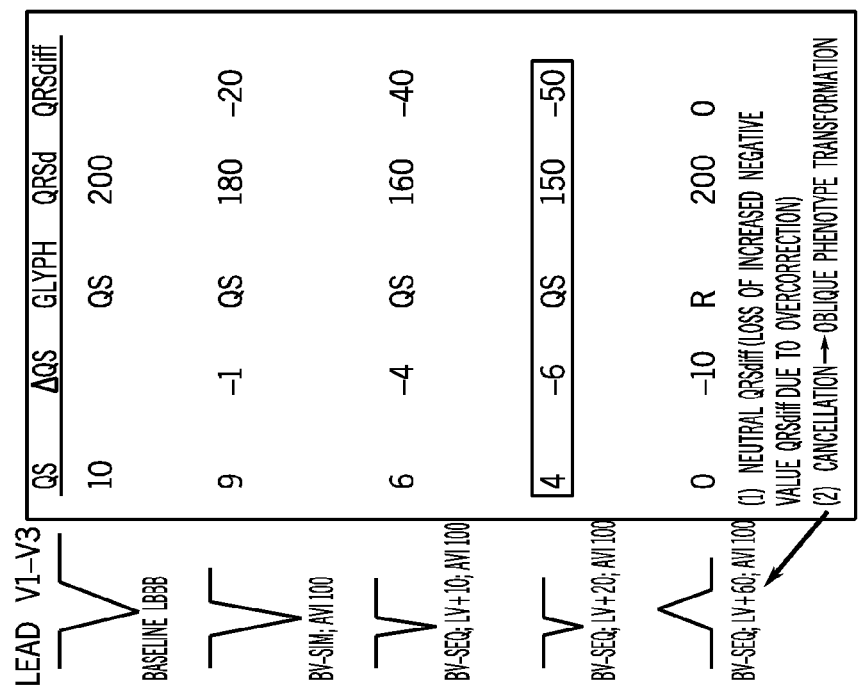
FIG. 15 is a pictorial illustration of an example activation sequence metrics log associated with the flow chart of FIG. 14.

First, simultaneous BV pacing is conducted (at process block 250), at a fixed pAVI (for example, at 100 ms, or 50% the iAVI). In some instances, the simultaneous BV pacing conducted from the identification process of FIG. 8 may be continued. An activation sequence metrics log, as shown in FIG. 15, including activation sequence output metrics or measures for a baseline waveform and the waveform created by the above simultaneous BV pacing, is then generated (process block 252). Such measures can include, but are not necessarily limited to, maximum QS wave amplitude from pivotal leads V1-V3, change in QS wave amplitude from the baseline, QRS glyph response, QRS duration and QRSdiff. In some instances, S wave metrics may be substituted for QS wave metrics in this process. According to the example activation sequence metrics log of FIG. 15, the baseline waveform exhibited a QS wave amplitude of 10 mV, a QS glyph, and a QRSd of 200 ms, as shown in row 1. The simultaneous BV pacing executed at process block 250 created a fusion waveform that exhibited a QS wave amplitude of 9 mV, a −1-mV change in QS wave amplitude, a QS glyph, a QRSd of 180 ms, and a QRSdiff of −20 ms, as shown in row 2.

Next, iterative sequential BV pacing is conducted (process block 254) at a fixed pAVI, such as 100 ms, where the timing of left ventricle stimulation is progressively advanced relative to right ventricle stimulation in incremental values (such as by +10 ms, +20 ms, +60 ms, etc.). Fusion waveform metrics at each iteration are identified and recorded in the activation sequence metrics log (process block 256). By way of example, FIG. 15 shows that sequential BV pacing with a +10-ms LV activation created a fusion waveform that exhibited a QS wave amplitude of 6 mV, a −4-mV change in QS wave amplitude, a QS glyph, a QRSd of 160 ms, and a QRSdiff of −40 ms, as shown in row 3. Sequential BV pacing with a +20-ms LV activation created a fusion waveform that exhibited a QS wave amplitude of 4, a −6-mV change in QS wave amplitude, a QS glyph, a QRSd of 150 ms, and a QRSdiff of −50 ms, as shown in row 4. Sequential BV pacing with a +60-ms LV activation created a fusion waveform that exhibited a QS wave amplitude of 0, a −10-mV change in QS wave amplitude, an R glyph, a QRSd of 200 ms, and a QRSdiff of 0 ms (indicating overcorrection), as shown in row 5. It may be noted that, in this example, during sequential pacing, QS regression is progressively amplified, indicating progressive reversal of baseline conduction defect (from anterior-posterior to posterior-anterior).

The activation sequence output metrics for each sequential BV pacing setting are then surveyed (process block 258) to identify the pacing control setting, in particular, the LV activation timing, that achieves the optimal fusion wavefront, as characterized by maximum evidence of positive change in activation (as indicated by regression in QRS glyphs), at the minimal paced QRSd, yielding the largest negative (increased) QRSdiff. Unlike oblique fusion responders, an increased QRSdiff is the only mandatory requirement for evidence of positive change in activation sequence during cancellation fusion. Further, unlike oblique fusion responders, the QRS glyph changes do not contain emergence of new QRS waveforms. Rather, QRS glyph changes are confined to regression of leftward and posteriorly directed forces (in particular QS, S waves). Therefore, for cancellation fusion responders, the best pacing control settings under these conditions are those which yield the largest negative value QRSdiff (or a minimum paced QRSd).

Thus, referring back to the example metrics log shown in FIG. 15, the sequential BV pacing with a +20-ms LV activation (shown in row 4) exhibited the optimal cancellation fusion phenotype wavefront, as determined by minimum QRSd and most negative QRSdiff. It is noted that, under this pacing parameter, the QRS glyph was unchanged, but amplitude has diminished by 60% and paced QRSd has diminished by 25% (hence causing "cancellation"). In this example, a lesser degrees of sequential biventricular pacing (+10-ms LV activation) yielded weaker evidence of positive change in activation (QS regression), longer paced QRSd and smaller (less negative) QRSdiff, while a larger degree of sequential biventricular pacing (+60-ms LV activated) yielded total activation reversal (indicated by monotonic R glyph), cancellation to oblique fusion phenotype transformation, greatest paced QRSd and a positive value QRSdiff. The larger degree also yielded an undesirable increase in total ventricular electrical asynchrony and complete abolition of the cancellation fusion phenotype.

Figure 16:
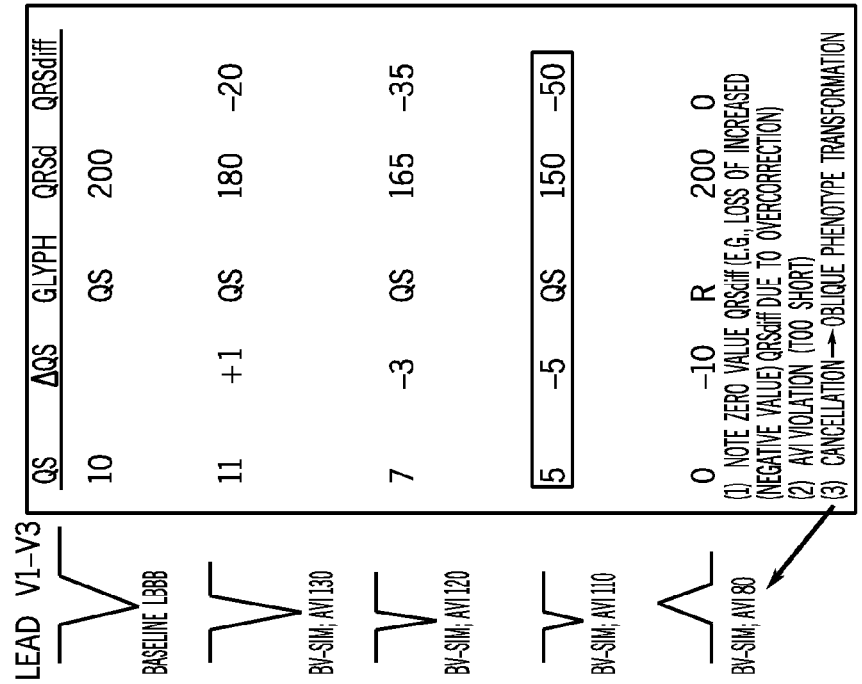
FIG. 16 is a pictorial illustration of another example activation sequence metrics log associated with the flow chart of FIG. 14.

Once the optimal LV activation timing is determined at process block 258, iterative simultaneous BV pacing is conducted (process block 260), where the pAVI is progressively changed in incremental values (such as 130 ms, 120 ms, 100 ms, 80 ms, etc.). Fusion waveform metrics at each iteration are identified and recorded (process block 262) in an activation sequence metrics log that includes at least baseline wavefront metrics (and may or may not include the metrics from sequential BV pacing). By way of example, FIG. 16 illustrates an activation sequence metrics log with a baseline waveform that exhibited a QS wave amplitude of 10 mV, a QS glyph, and a QRSd of 200 ms, as shown in row 1. Simultaneous BV pacing with a 130-ms pAVI created a cancellation fusion waveform that exhibited a QS wave amplitude of 11 mV, a 1-mV change in QS wave amplitude, a QS glyph, a QRSd of 180 ms, and a QRSdiff of −20 ms, as shown in row 2. Simultaneous BV pacing with a 120-ms pAVI created a cancellation fusion waveform that exhibited a QS wave amplitude of 7 mV, a −3-mV change in QS wave amplitude, a QS glyph, a QRSd of 165 ms, and a QRSdiff of −35 ms, as shown in row 3. Simultaneous BV pacing with a 110-ms pAVI created a cancellation fusion waveform that exhibited a QS wave amplitude of 5 mV, a −5-mV change in QS wave amplitude, a QS glyph, a QRSd of 150 ms, and a QRSdiff of −50 ms, as shown in row 4. Simultaneous BV pacing with an 80-ms pAVI created a cancellation to oblique fusion waveform transformation that exhibited QS wave elimination (as indicated by a QS wave amplitude of 0 mV, a −10-mV change in QS wave amplitude) a newly emerged R glyph, a QRSd of 200 ms, and a QRSdiff of 0 ms, as shown in row 5.

The activation sequence output metrics for each simultaneous pacing setting are then surveyed (process block 264) to identify the pacing control setting, in particular, pAVI, that achieves the optimal fusion wavefront, as characterized by maximum evidence of positive change in activation (as indicated by the QRS glyphs), at the minimal paced QRSd, yielding the largest negative (increased) QRSdiff. As noted above, since cancellation fusion wavefronts may not exhibit a positive change in activation sequence accompanied by a neutral or decreased QRSdiff or observable regression in QRS glyphs, the optimal pacing control settings under such conditions may be those which yield the most negative QRSdiff. Thus, referring back to the example metrics log in FIG. 16, the simultaneous BV pacing with a 100-ms pAVI (illustrated in row 4) exhibited the optimal cancellation fusion waveform, as determined by the minimum QRSd and most negative QRSdiff.

Once the optimal pAVI setting is determined in process block 264, an additional pAVI setting check is performed (process block 266). This additional check ensures that the optimal pAVI determined at process block 242 satisfies conditions of atrial sensing and atrial pacing. For example, a chosen pAVI may not satisfy such conditions if the duration is too short (such as the 80-ms pAVI from row 5 of FIG. 16). If the chosen pAVI does not satisfy such conditions, the "next best" pAVI is chosen through examination of the activation sequence output metrics (process block 268). If the pAVI does satisfy atrial sensing and atrial pacing conditions, the chosen LV activation timing and pAVI are used as final pacing control settings for CRT (process block 270). Thus, in accordance with the above method, the final pacing control settings for optimal cancellation fusion may be those which satisfy the following conditions: maximize evidence of positive change in activation sequence, illustrated by regression of posteriorly directed forces (QS, S waves) in pivotal leads V1-V3; minimized paced QRSd; maximize negative (increased) QRSdiff; and satisfy optimal pAVI requirements under conditions of atrial sensing and pacing.

As described above with respect to oblique fusion, it is recognized that the change in activation sequence metrics during titration of pacing control parameters (pAVI, sequential BV stimulation, and other manipulations known to those skilled in the art) display generally predictable trends and behaviors but also demonstrate substantial intra-patient and inter-patient heterogeneity. For example, in some patients, a specific combination of pAVI and sequential BV pacing will be necessary to achieve optimal wavefront fusion. Likewise, in otherwise similar patients, a variation of only the pAVI during simultaneous BV pacing may achieve optimal cancellation fusion. It is further possible that in other patients, a specific combination of LV electrode pairs, pAVI and sequential biventricular pacing will be necessary to achieve optimal wavefront fusion.

In addition, it is understood that the activation sequence metrics displayed in FIGS. 15 and 16, though accurate for determining optimal wavefront fusion, are merely representative. A multiplicity of additional metrics sufficient to permit precise quantification of changes in the QRS glyph response during the fusion titration sequence may also be collected. It is similarly understood that a parallel activation sequence change metrics log may also be constructed using similar methods and logic for the CIED glyphs that serves as quantitative surrogates for critical surface ECG glyphs. Furthermore, in some instances, the above two titration processes may be executed in parallel to further refine optimal pacing control parameters for the individual patient, as discussed above with respect to oblique fusion.

Figure 17:
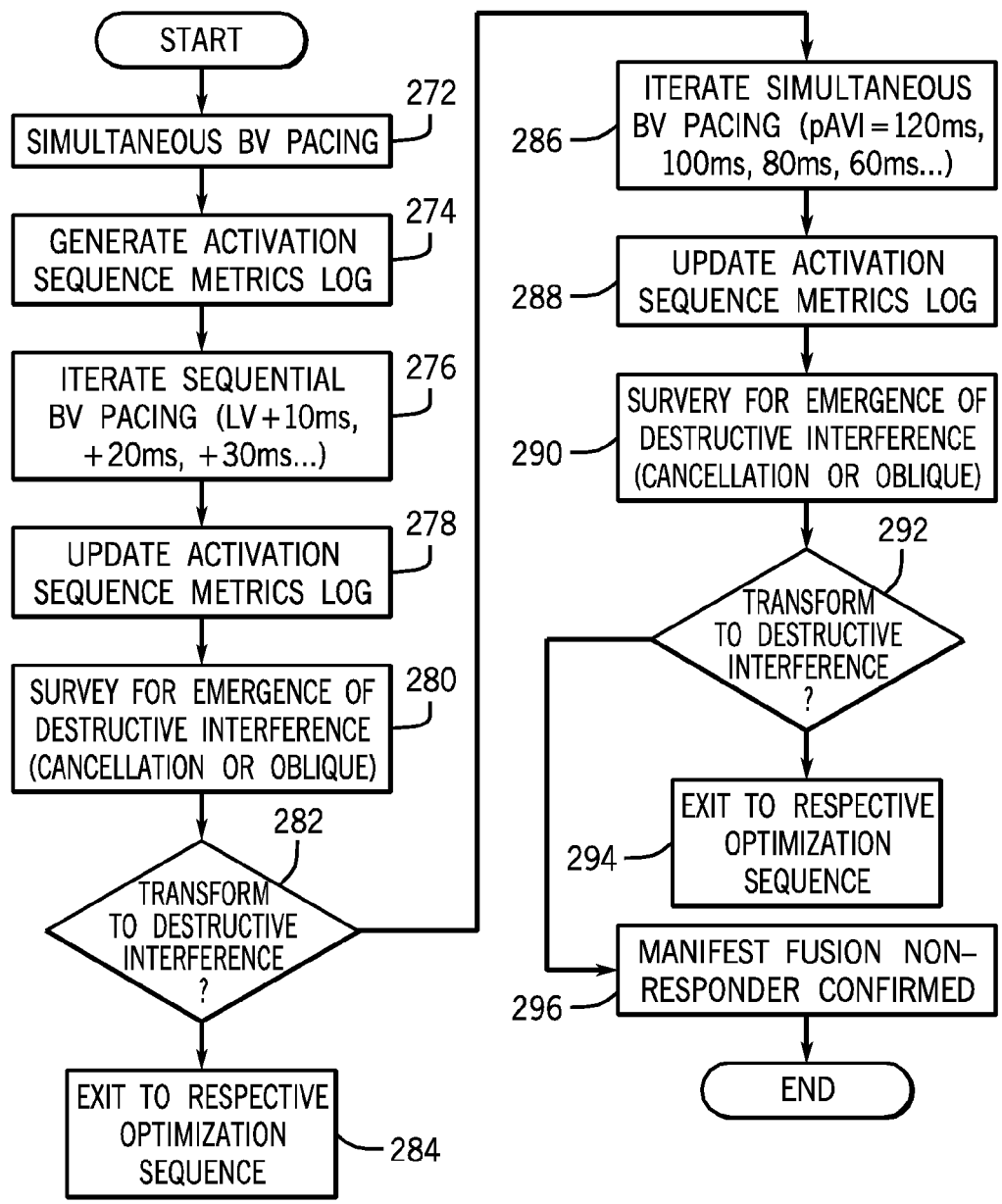
FIG. 17 is a flowchart setting forth the steps of an exemplary method for titrating cardiac resynchronization therapy pacing parameters in relation to a recognized summation fusion response phenotype.

Continuing with the logic and analytic approaches described above, an exemplary process for identifying concealed fusion responder phenotypes is provided in FIG. 17. The general goal of this process is to identify patients with false forms of destructive interference masquerading as a fusion non-responder phenotype. Generally, this may be achieved using changes to pacing control parameters to induce transformation to oblique fusion or cancellation fusion responders. In particular, changes to the timing of biventricular pacing (such as sequential ventricular stimulation) resulting in asynchronous wavefront frequency timing, or change in path length (such as alternate stimulation pathway using a multielectrode LV lead) may reveal an oblique or cancellation fusion response phenotype concealed by simultaneous biventricular stimulation. This exploits the observation that sequential BV stimulation may overcome factors known to inhibit positive change in activation sequence during simultaneous BV pacing, including differential bidirectional ventricular conduction times, fixed conduction blocks (from scar volume), functional conduction blocks, left ventricular capture latency, and/or other factors known to those skilled in the art. It is understood that the process steps of FIG. 17 described below broadly summarize this approach and are not exhaustive.

Figure 18:
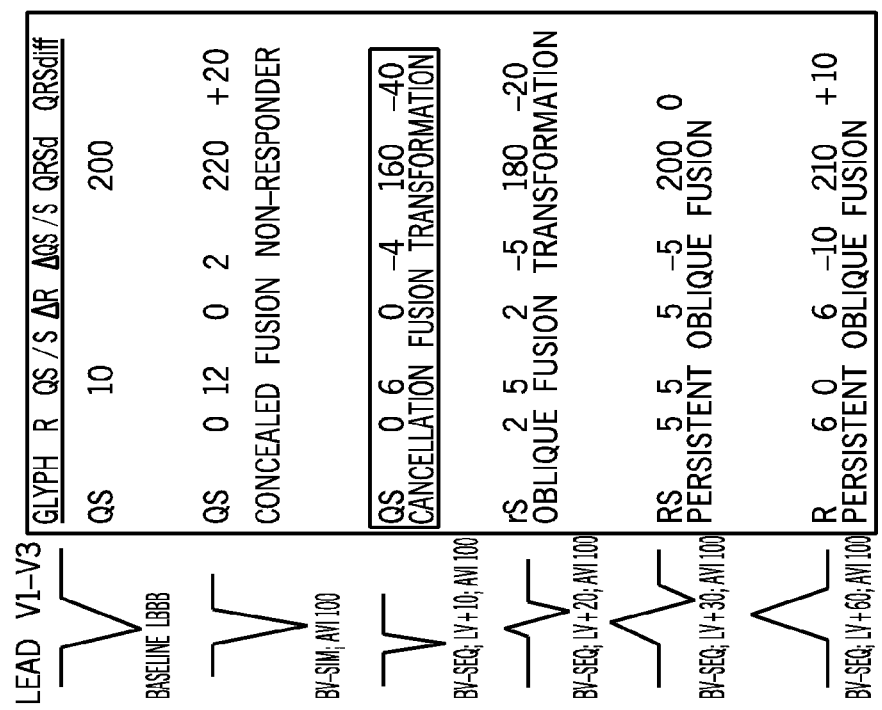
FIG. 18 is a pictorial illustration of an example activation sequence metrics log associated with the flow chart of FIG. 17.

First, simultaneous BV pacing is conducted (at process block 272), at a fixed pAVI (for example, at 100 ms, or 50% the iAVI). In some instances, the simultaneous BV pacing conducted from the identification process of FIG. 8 may be continued. An activation sequence metrics log, as shown in FIG. 18, including activation sequence output metrics or measures for a baseline waveform and the waveform created by the above simultaneous BV pacing, is then generated (process block 274). Such measures can include, but are not necessarily limited to, QRS glyph response, maximum QS and R wave amplitudes from pivotal leads V1-V3, change in QS and R wave amplitudes from the baseline, QRS duration and QRSdiff. In some instances, S wave metrics may be substituted for QS wave metrics in this process. According to the example activation sequence metrics log of FIG. 18, the baseline waveform exhibited a QS glyph, an R wave amplitude of 0 mV, a QS amplitude of 10 mV, and a QRSd of 200 ms, as shown in row 1. The simultaneous BV pacing executed at process block 272 created a fusion waveform that exhibited a QS glyph, a QS wave amplitude of 12 mV, a 0-mV change in R wave amplitude, a 2-mV change in QS wave amplitude, a QRSd of 220 ms, and a QRSdiff of +20 ms, as shown in row 2.

Next, iterative sequential BV pacing is conducted (process block 276) at a fixed pAVI, such as 100 ms, where the timing of left ventricle stimulation is progressively advanced relative to right ventricle stimulation in incremental values (such as by +10 ms, +20 ms, +30 ms, +60 ms, etc.). Fusion waveform metrics at each iteration are identified and recorded in the activation sequence metrics log (process block 278). By way of example, FIG. 18 shows that sequential BV pacing with a +10-ms LV activation created a fusion waveform that exhibited a QS glyph, a QS wave amplitude of 6 mV, a 0-mV change in R wave amplitude, a −4-mV change in QS wave amplitude, a QRSd of 160 ms, and a QRSdiff of −40 ms, as shown in row 3. Sequential BV pacing with a +20-ms LV activation created a fusion waveform that exhibited an rS glyph, an R wave amplitude of 2 mV, a QS wave amplitude of 5 mV, a 2-mV change in R wave amplitude, a −5-mV change in QS wave amplitude, a QRSd of 180 ms, and a QRSdiff of −20 ms, as shown in row 4. Sequential BV pacing with a +30-ms LV activation created a fusion waveform that exhibited an RS glyph, an R wave amplitude of 5 mV, a QS wave amplitude of 5 mV, a 5-mV change in R wave amplitude, a −5-mV change in QS wave amplitude, a QRSd of 200 ms, and a QRSdiff of 0 ms, as shown in row 5. Sequential BV pacing with a +60-ms LV activation created a fusion waveform that exhibited an R glyph, an R wave amplitude of 6 mV, e, a 6-mV change in R wave amplitude, elimination of the QS wave (indicated by a −10-mV change in QS wave amplitude), a QRSd of 210 ms, and a QRSdiff of +10 ms, as shown in row 6.

The sequential BV pacing from process block 276 may induce a phase shift, which can enhance fusion activation by inducing oblique or cancellation fusion. Thus, the activation sequence output metrics for each sequential BV pacing setting are then surveyed (process block 280) to identify emergence of a concealed oblique or cancellation fusion phenotype. For example, referring back to FIG. 18, BV sequential pacing with a +10-ms LV activation (shown in row 3) exhibits a transformation to a cancellation fusion phenotype. This is exhibited by a regression in all waveform components (most notably a 40% reduction in QS amplitude), a 40% reduction in QRSd, yielding QRSdiff of −40 ms, indicating a substantial reduction in total ventricular asynchrony. Furthermore, continuing sequential biventricular pacing with greater LV activation timing, a further transformation to the oblique fusion phenotype is induced, as shown in row 4 in the metrics log of FIG. 18. This is exhibited by QRS glyph change from QS to rS, reflecting emergence of anteriorly directed forces (R wave). Further increases in sequential biventricular pacing advance the persistent oblique fusion phenotype, with expected QRS glyph changes, increase in QRSd and reduction in QRSdiff. In addition, in this example, maximum evidence of positive change in activation (QRS glyphs response) at the minimal paced QRSd yielding the largest negative (increased) QRSdiff is observed during BV sequential pacing at +20-ms LV activation (shown in row 3), when transformation to the cancellation fusion phenotype occurs.

If a transformation from fusion non-responder to oblique or cancellation fusion phenotype is observed (as determined at process block 282), the respective optimization sequence, as described above, is then executed (process block 284). In some instances, activation sequence output metrics may be recorded and assessed after each iteration so that, as soon as a oblique or cancellation fusion phenotype is observed, the respective optimization process may be executed (without having to continue with further iterations).

If a fusion non-responder phenotype persists (as determined at process block 282), iterative simultaneous BV pacing is conducted (process block 286), where the pAVI is progressively changed in incremental values (such as 120 ms, 110 ms, 100 ms, etc.). Fusion waveform metrics at each iteration are identified and recorded (process block 288) in an activation sequence metrics log that includes at least baseline wavefront metrics. Similar to that described above, the activation sequence output metrics for each simultaneous BV pacing setting are then surveyed (process block 290) to identify emergence of a concealed oblique or cancellation fusion phenotype. If a transformation from fusion non-responder to oblique or cancellation fusion phenotype is observed (as determined at process block 292), the respective optimization sequence, as described above, is then executed (process block 294).

If a fusion non-responder phenotype persists (as determined at process block 292), a manifest fusion non-responder phenotype is confirmed (process block 296) and no further manipulations of pacing control parameters are applied, that is, further efforts to induce a positive change in activation with pacing control parameters using biventricular pacing are not conducted.

Figure 19:
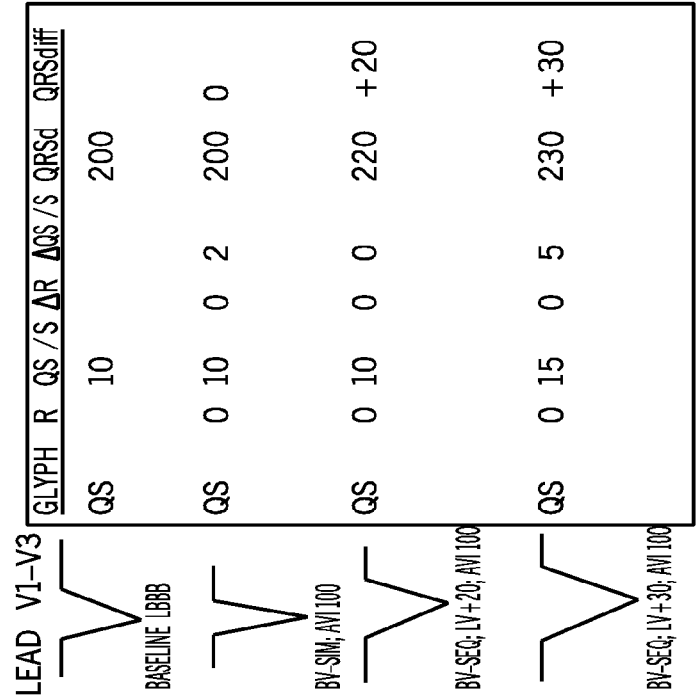
FIG. 19 is a pictorial illustration of another example activation sequence metrics log associated with the flow chart of FIG. 17.

FIG. 19 illustrates an example activation sequence metrics log including activation sequence output metrics or measures (for example, from process blocks 272-280, described above), indicative of a manifest fusion non-responder. The baseline waveform of FIG. 19 exhibited a QS glyph, a QS amplitude of 10 mV, and a QRSd of 200 ms, as shown in row 1. Simultaneous BV pacing, with a fixed 100-ms pAVI, created a fusion waveform that exhibited a persistent QS glyph, a QS wave amplitude of 12 mV, a 2-mV change in QS wave amplitude, a QRSd of 200 ms, and a QRSdiff of 0 ms, as shown in row 2. Sequential BV pacing at LV +20 ms, with a fixed 100-ms pAVI, created a fusion waveform that exhibited a QS glyph, a QS wave amplitude of 10 mV, a 0-mV change in QS wave amplitude, a QRSd of 220 ms, and a QRSdiff of +20 ms, as shown in row 3. Sequential BV pacing at LV +30 ms, with a fixed 100-ms pAVI, created a fusion waveform that exhibited a persistent QS glyph, a QS wave amplitude of 15 mV, a 5-mV change in QS wave amplitude, a QRSd of 230 ms, and a QRSdiff of +30 ms, as shown in row 4.

As shown in the example metrics log of FIG. 19, simultaneous BV pacing caused the baseline LBBB QRS glyph to be amplified (in particular, QS pattern persisted, Q amplitude increased by 20%, QRSd and QRSdiff were unchanged). Continuing with sequential biventricular pacing, the amplification process was enhanced, exhibited by progressive increase in QRS glyph pattern (in particular, QS amplitude), increased QRSd and reduced QRSdiff. This pattern satisfies the definition of conduction delay stacking, as described above. In some instances, upon determination of conduction delay stacking, the above process proceeds straight to process block 296 and no further manipulations of pacing control parameters are applied.

If a fusion non-responder phenotype persists despite manipulation of pacing control parameters (if a manifest fusion non-responder phenotype is recognized) at process block 296, alternate strategies to restore ventricular resynchronization are necessary, including, but not limited to, selection of a new LV pacing site in order to change paced ventricular conduction paths. This may be achieved by repositioning of the LV pacing lead or selection of alternate LV electrodes from a multielectrode LV lead, as described below. The change in conduction path may favorably affect the resulting paced ventricular activation sequence and reveal a concealed oblique or cancellation fusion phenotype. For example, a change in path length could cause a phase shift such that the activation wavefronts move into anti-phase.

Figure 20:
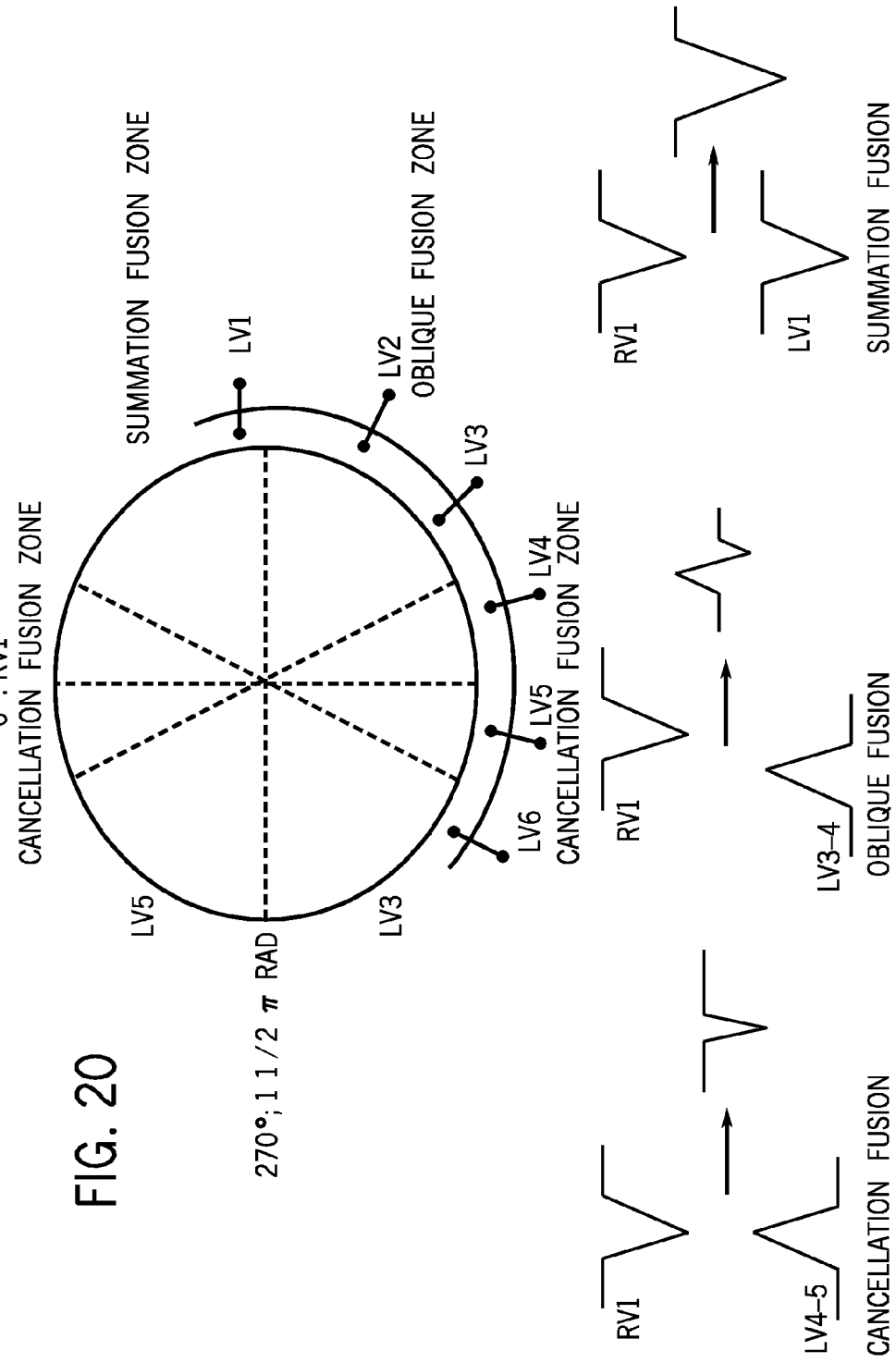
FIG. 20 is a schematic illustration of fusion response phenotypes in relation to cardiac stimulation sites from a multielectrode left ventricle lead.

Referring to FIG. 20, a multielectrode LV lead in accordance with the present invention, including electrodes LV1, LV2, LV3, LV4, LV5, and LV6, is schematically shown traversing the lateral wall of the LV hemisphere. The multielectrode LV lead (in which electrodes may be used in pairs or across chambers) may be specifically implemented to select the patient-specific optimal LV stimulation site at implant, enhance fusion activation phenotype recognition, modify optimization in fusion responders, and transform fusion non-responders to responder phenotypes, thereby contributing to increased odds of reverse remodeling and clinical improvement. As discussed above, varying LV stimulation sites can yield different activation fusion response phenotypes by altering the form of wavefront interference during biventricular pacing. This effect relates to changes in wavefront opposition, conduction path length, and other physical properties of wavefront propagation.

Figures 21, 22:
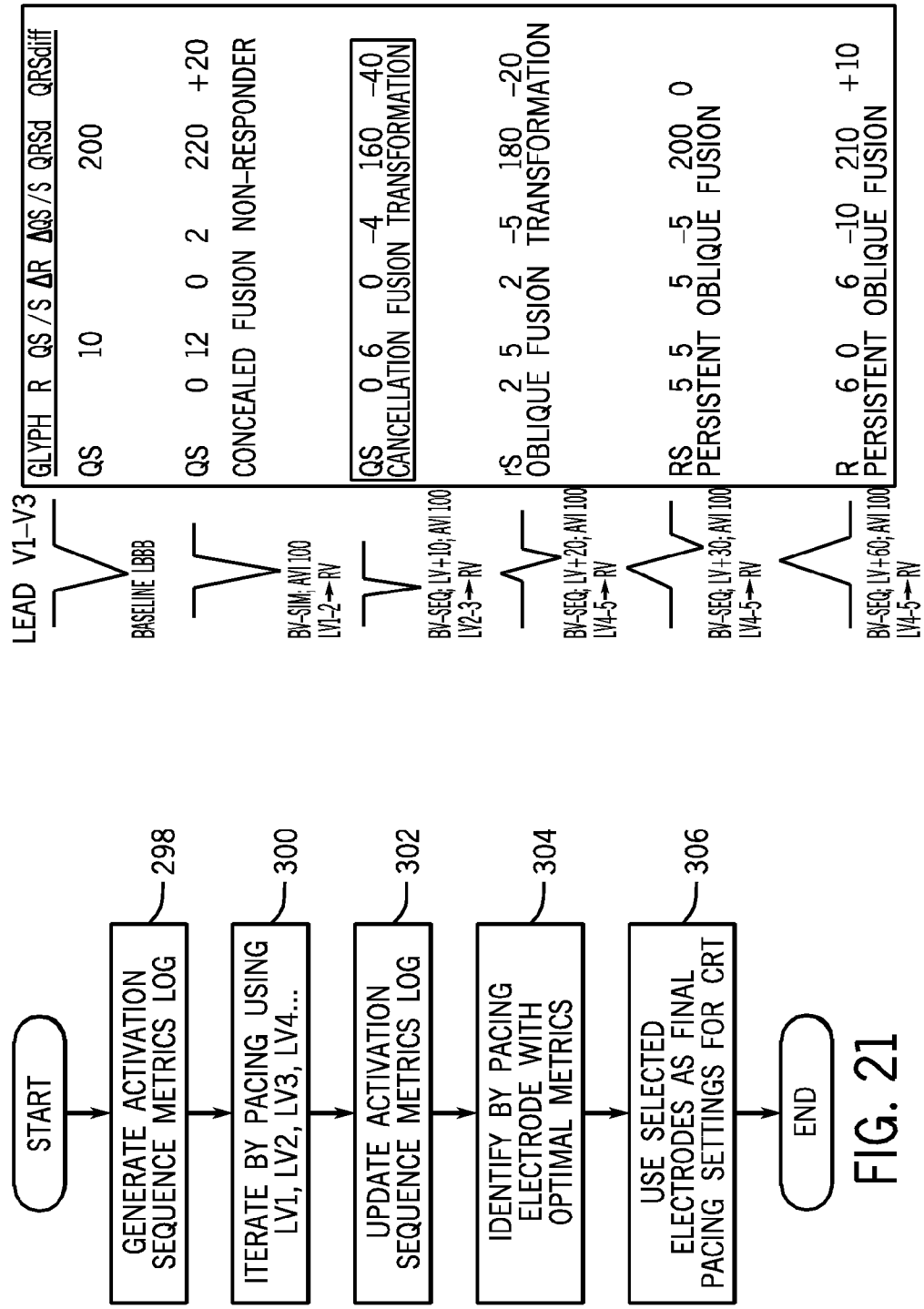
FIG. 21 is a flowchart setting forth the steps of an exemplary method for titrating cardiac resynchronization therapy pacing parameters and pacing stimulation sites in relation to a recognized summation fusion response phenotype.
FIG. 22 is a pictorial illustration of an example activation sequence metrics log associated with the flow chart of FIG. 21.

Accordingly, continuing with the logic and analytic approaches described above, an exemplary process for transformation of a concealed fusion responder through conduction path adjustment, via a multielectrode LV lead, is provided in FIG. 21. The process includes generating an activation sequence metrics log with baseline waveform metrics (process block 298). Simultaneous and/or sequential BV pacing is then conducted using different sets of electrode pairs from the multielectrode LV lead (process block 300). Fusion waveform metrics for each electrode pair used are identified and recorded in the activation sequence metrics log (process block 302). The fusion waveform metrics are then surveyed (process block 304) to determine which electrode pair exhibits a transformation to cancellation or oblique fusion, or further, which electrode pair exhibits optimal cancellation or oblique fusion. The chosen LV electrode is then applied to final pacing control settings for CRT (process block 306).

By way of example, FIG. 22 illustrates a generated activation sequence metrics log with a baseline waveform that exhibits a QS glyph, a QS amplitude of 10 mV, and a QRSd of 200 ms, as shown in row 1. Simultaneous BV pacing, with a fixed 100-ms pAVI, using electrode pair LV1-LV2, created a fusion waveform that exhibited a QS glyph, an R wave amplitude of 0 mV, a QS wave amplitude of 12 mV, a 2-mV change in QS wave amplitude, a QRSd of 220 ms, and a QRSdiff of +20 ms, as shown in row 2. Simultaneous BV pacing, with a fixed 100-ms pAVI, using electrode pair LV2-LV3, created a fusion waveform that exhibited a QS glyph, a QS wave amplitude of 6 mV, a −4-mV change in QS wave amplitude, a QRSd of 160 ms, and a QRSdiff of −40 ms, as shown in row 3. Simultaneous BV pacing, with a fixed 100-ms pAVI, using electrode pair LV4-LV5, created a fusion waveform that exhibited an rS glyph, an R wave amplitude of 2 mV, a QS wave amplitude of 5 mV, a 2-mV change in R wave amplitude, a −5-mV change in QS wave amplitude, a QRSd of 180 ms, and a QRSdiff of −20 ms, as shown in row 4. Sequential BV pacing, with a fixed 100-ms pAVI and LV +20 ms, using electrode pair LV4-LV5, created a fusion waveform that exhibited an RS glyph, an R wave amplitude of 5 mV, a QS wave amplitude of 5 mV, a 5-mV change in R wave amplitude, a −5-mV change in QS wave amplitude, a QRSd of 200 ms, and a QRSdiff of 0 ms, as shown in row 5. Sequential BV pacing, with a fixed 100-ms pAVI and LV +40 ms, using electrode pair LV4-LV5, created a fusion waveform that exhibited an R glyph, an R wave amplitude of 6 mV, a QS wave amplitude of 0 mV, a 6-mV change in R wave amplitude, a −10-mV change in QS wave amplitude, a QRSd of 210 ms, and a QRSdiff of +10 ms, as shown in row 6.

Using the example waveform metrics of FIG. 22, simultaneous BV pacing using LV electrode pair LV1-LV2 caused the baseline LBBB QRS glyph to be amplified (in particular QS pattern persisted, Q amplitude increased by 20%, and QRSd increased by 20%, causing a positive QRSdiff, indicating increase in total ventricular asynchrony). Simultaneous BV pacing using LV electrode pair LV2-LV3 caused a transformation to a cancellation fusion phenotype. This is exhibited by a regression in all waveform components (most notably a 40% reduction in QS amplitude) and a 40% reduction in QRSd, yielding QRSdiff of −40, indicating a substantial reduction in total ventricular asynchrony. Simultaneous biventricular pacing with LV electrode pair LV4-LV5 caused a further transformation to an oblique fusion phenotype. This is exhibited by QRS glyph change from QS to rS, reflecting emergence of anteriorly directed forces (R wave). The addition of sequential biventricular pacing with LV electrode pair LV4-LV5 advanced the persistent oblique fusion phenotype, with QRS glyph changes (baseline QS to RS and R), increase in QRSd and reduction in QRSdiff. Thus, in this example, optimal wavefront fusion, characterized by maximum evidence of positive change in activation (QRS glyphs response) at the minimal paced QRSd yielding the largest negative (increased) QRSdiff, is observed during BV simultaneous pacing using electrode pair LV2-LV3, when transformation to the cancellation fusion phenotype occurred.

In some instances, a similar flow process may be conducted during manipulation of the pAVI while holding simultaneous biventricular pacing constant and varying LV electrode pairs. Furthermore, other variations of this approach are readily appreciated by those skilled in the art. In any case, once a transformation from fusion non-responder to oblique or cancellation fusion phenotype is observed, transfer to the appropriate optimization sequence can occur. In addition, in some instances, the process of FIG. 21 above may be used to obtain an optimized set of activation fusion response metrics not achievable if the LV stimulation were limited to a different site.

It is another aspect of the multielectrode LV lead of the present invention to function as an indicator of change in activation sequence. Since LV lead placement targets the posterior wall of the left ventricle, EGMs generated between electrodes on the LV lead and an anteriorly positioned electrode (such as RV coil, SVC coil, housing of the pulse generator) could provide accurate information regarding activation wavefront propagation in the anterior-to-posterior directions. In particular, individual LV electrodes or pairs of LV electrodes not in use for pacing stimulation could additionally be applied for this purpose. These EGMs could serve as surrogates for surface QRS glyphs to characterize and titrate activation fusion phenotypes and associated electrical resynchronization metrics on a patient-specific basis.

It is noted that some conventional CRT systems may employ multielectrode LV leads. However, in these systems, their purpose is simply to offer additional alternative stimulation sites in order to overcome undesirable biomechanical attributes localized to specific sites within the target LV vein. Such alternative stimulation sites can be tested and applied noninvasively by reprogramming through the CIED. Therefore, the intent of conventional multielectrode lead design in common usage is to offer the option of alternative stimulation sites without necessitating surgical repositioning or replacement of the initially implanted LV lead. While this arrangement is potentially useful for the intended purpose of overcoming undesirable physical stimulation characteristics (such as extra-cardiac, that is, phrenic nerve stimulation, undesirably high ventricular pacing thresholds and the like), this arrangement does not advance the primary therapy goal of CRT which is recognition and informed correction of ventricular conduction delay, indicated by specific activation wavefront response patterns, as discussed above. Furthermore, this use of a multielectrode LV lead is fundamentally no different than any conventional pacing lead, namely, to deliver pacing stimuli that result in cardiac stimulation unqualified for the consequences of that specific stimulation on the ventricular conduction sequence.

In light of the methods described above with reference to FIGS. 10-22, the activation change metrics log can be used to numerically quantify optimal activation output parameters, and one or more paced QRS glyphs indicative of patient-specific optimal ventricular activation fusion for template matching can be identified. The corresponding activation output metrics for each of these QRS glyphs provides for precise duplication of the magnitude relationships among QRS component waveforms, which expresses the extent to which activation has been positively modified. Therefore, not only is the QRS template during optimal oblique or cancellation fusion activation examined, but also the quantitative relationships between the component waveforms, paced QRSd, and QRSdiff. The QRS glyph template, CIED-based EGM glyph surrogates, the glyph-specific corresponding activation output metrics, and the corresponding pacing control parameters can form the integrated basis of the methods of the present invention for generating automatic and updating of patient-specific optimal ventricular activation fusion. In general, the interactive relationship between these operating parameters is summarized as follows: the paced QRS glyphs and CIED-based EGM surrogates provide patient-specific evidence for positive change in activation sequence; the quantitative activation output metrics identify the patient-specific paced QRS glyphs and CIED-based EGM surrogates during optimal ventricular activation fusion; these activation output metrics and the associated critical pacing control parameters are used to titrate and periodically update patient-specific fusion patterns; both glyph template matching and activation fusion metrics are used for the patient-specific titrating and updating methods described herein because the relationship between these parameters is unique to the individual patient; and glyph template matching and activation fusion metrics provide mechanisms for internal validation of the titration process. As an example, it is expected that a decreased (more positive) QRSdiff will be recorded in some oblique fusion responders, despite a positive change in activation sequence. The corresponding glyph templates provide validation that the increase in total ventricular electrical asynchrony is due to a positive change in activation sequence accompanied by slow propagation of competitive asymmetrically opposed wavefronts. In this manner, the glyph templates provide evidence that electrical resynchronization with slow conduction has occurred despite decreased (more positive) QRSdiff, rather than a negative change in activation sequence, as observed during summation fusion failure.

In light of the descriptions above, the present invention provides an ECG-based symbol language to recognize, optimize, and automatically titrate specific ventricular activation fusion response phenotypes. This symbol language is utilized in a variety of ways to assess, update, instruct and confirm device pacing control parameters relevant to generation of targeted ventricular activation fusion response patterns. In accordance with the present invention, such assessments can be periodically conducted in several ways, as summarized in FIG. 22.

In one approach, the process is entirely CIED-based. This approach may utilize a separate EGM input system not involved with pacing stimulus delivery. The CIED-based EGM surrogates for optimal ventricular activation fusion could then be compared against baseline templates in real-time. Such separate EGM inputs for biventricular paced template "viewing" could utilize subcutaneous sources, as further described below, and intracardiac sources (such as a multielectrode LV lead, as described above)

Additionally, the process can be implemented in parallel as a User Interface application (UI app) in an external programmer serving one or more of the following purposes: (1) as a patient selection guide by using the UI app-baseline ECG interaction to characterize substrate conditions for reverse remodeling and predict odds of reverse remodeling based on various assumptions (lead position, ECG fusion phenotype); (2) as an implant guide by using the UI app-LV lead positioning interaction for manipulation of ECG fusion phenotype to identify ECG phenotype by lead site, electrode pair, and cross-chamber electrode combinations, modify ECG phenotype by choosing different lead site, multielectrode lead, or cross-chamber electrode combinations, modify ECG phenotype by manipulation of RV stimulation sites; (3) for pre-discharge after CRT implantation by using the UI app-device interaction to titrate patient-specific optimal ECG fusion phenotype; (4) for long-term follow-up by using the UI app-device interaction to identify changes in conditions that affect optimal ECG phenotype and adjust titration for changing patient conditions Periodic assessments can also be conducted during communication with an external programmer. In this approach, parameters of the patient-specific optimized activation fusion response phenotype at implant, and/or last follow-up, can be stored in individual patient files on the programmer. Communication with the CIED can establish a link to the specific patient file and initiate software for template comparisons (morphology analysis). Quantitative comparisons can be made between QRS glyphs on the surface ECG in real-time (during biventricular pacing) and QRS glyphs reflecting the optimized activation fusion phenotype from implant or last follow-up. Similarly, quantitative comparisons can be made between CIED-based EGM glyph surrogates for surface activation. In this fashion, the primary data source for titrating evidence of optimized ventricular fusion, the surface ECG, is evaluated rather than CIED-based EGM surrogates alone. As discussed above, the surface ECG may be reduced to pivotal leads, thereby increasing ease of use during follow-up.

Periodic assessments can also be conducted automatically during routinely scheduled or triggered communication with a multiple server-based computational resource accessed through a digital network linked to the CIED through a portable or bed-side communication station. Server-based software can conduct morphologic and quantitative comparison of CIED-based EGM surrogates of patient-specific activation fusion response phenotypes. Recognition of an important change in the activation fusion response phenotype could generate an electronic "flag" for physician reporting, or trigger an automatic recycle of the optimization sequence in the CIED immediately or in response to the next programmer interaction. An advantage of such a "cloud-based" strategy is the capacity for greater computational resources as compared to the CIED or programmer based strategies. Another advantage common to the programmer-based or "cloud-based" approach is that it eliminates the need for a separate CIED-EGM input system not dedicated to pacing stimulation delivery.

Figure 23:
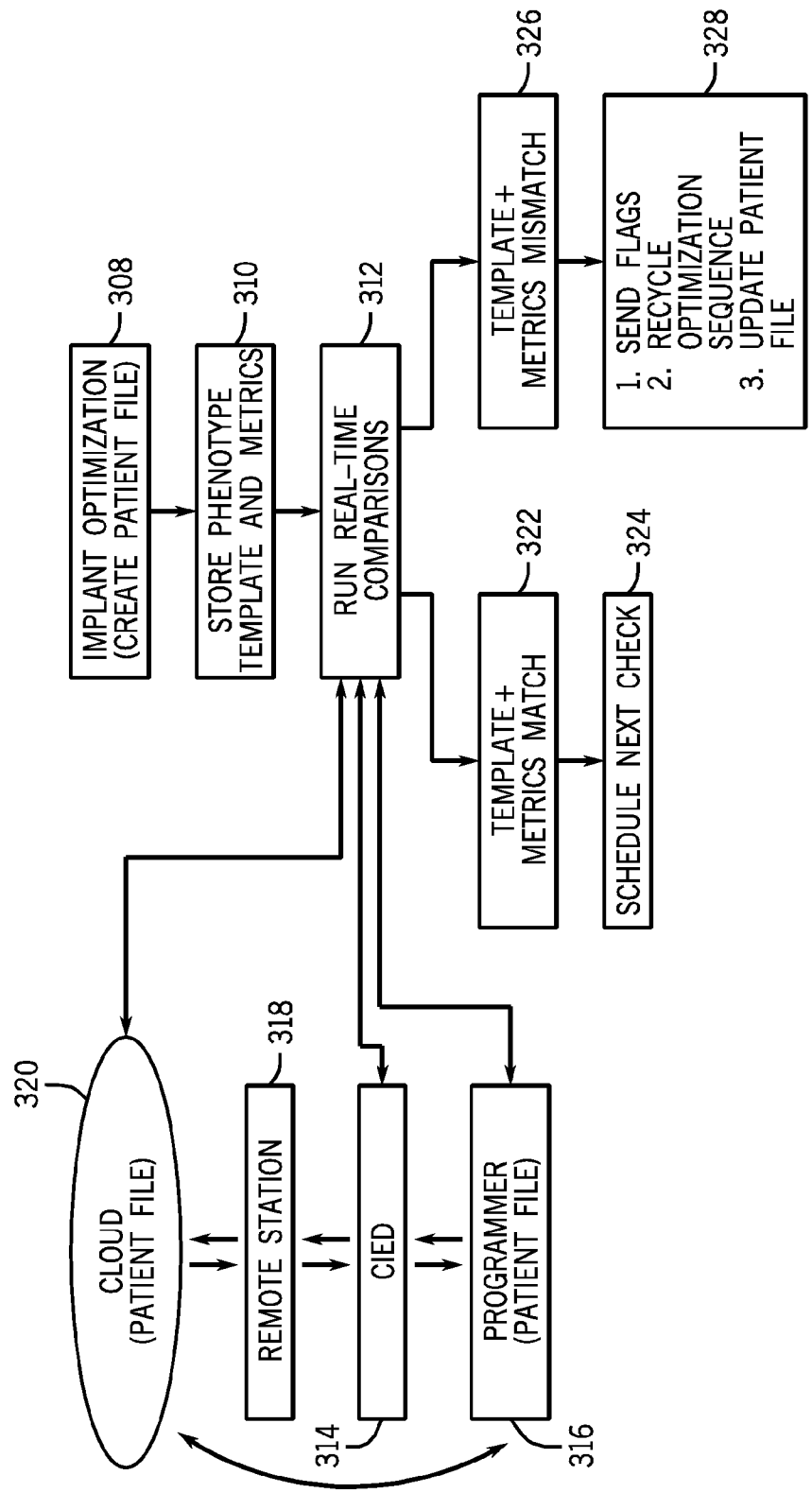
FIG. 23 is a flowchart setting forth the steps of an exemplary method for periodic evaluation of fusion response phenotypes and optimal pacing parameters during cardiac resynchronization therapy.

Thus, a general method for evaluation, as shown in FIG. 23, can include creating a patient file with optimized parameters at implant (process block 308), storing a phenotype template and wavefront metrics (process block 310), and periodically running real-time comparisons (process block 312), for example using the CIED 314, an external programmer 316, a remote station 318 and/or other cloud-based approaches 320. If the stored template and wavefront metrics match the current phenotype and wavefront metrics (process block 322), a next check is scheduled (process block 324). If there is a mismatch (process block 326), a new optimization sequence is executed, for example in accordance with one or more described methods of the present invention, and the patient file is updated with a new phenotype template and wavefront metrics (process block 328).

As discussed above, it is an aspect of this invention to apply CIED-based EGM surrogates for surface ECG activation patterns (QRS glyphs) in these tasks. Currently, EGMs conventional CRT systems are derived from one or more intracardiac EGMs. While these intracardiac EGMs can be correlated with signature changes in amplitude, duration and directionality as relevant surface ECG signals, they may be limited as a more localized point of view that is further constrained by the necessary anatomic limitations of the cardiac space. According to some implementations of the present invention, a subcutaneous recording source can be used to overcome these anatomic limitations, more closely approximate one or more surface ECG signals, and provide greater resolution on activation wavefront propagation and shape.

Figure 24:
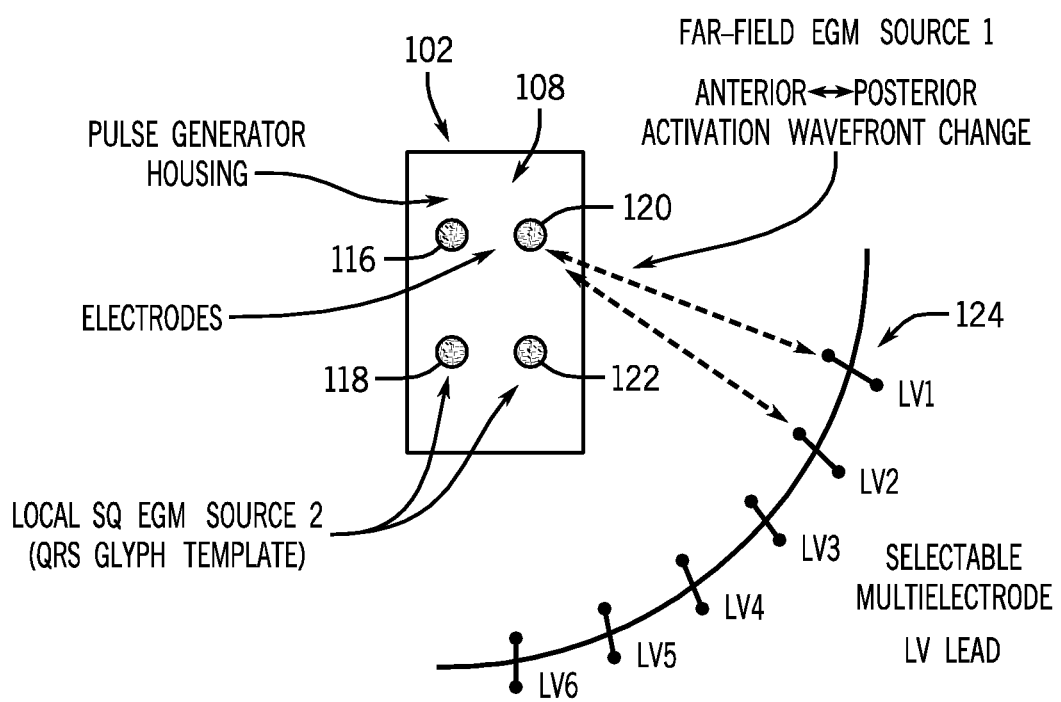
FIG. 24 is a pictorial illustration of an exemplary pacing generator housing of a cardiac implantable electronic device ("CIED") employed when practicing embodiments of the present invention.

For example, the housing 108 of a CRT pulse generator 102, as shown in FIGS. 1 and 24, can act as a subcutaneous recording source. Since the CRT pulse generator 102 is typically implanted in the left superior chest, an opportunity to closely approximate pivotal ECG leads V1-V3 is recognized. A multiplicity of electrodes 116-122 on the pulse generator 102 could be used in pairs (for local recording) or in combination with selected intracardiac electrodes (for far-field recording). In particular, the use of a subcutaneous electrode and one or more selectable electrode pairs on a multielectrode LV lead 124 can provide high resolution for activation sequence change in the anterior-to-posterior direction. Thus, in some implementations, a multielectrode LV lead and a subcutaneous recording source may function as integral parts of the activation fusion optimization processes described above, rather than merely acting as a delivery system for pacing stimulation.

Figure 25:
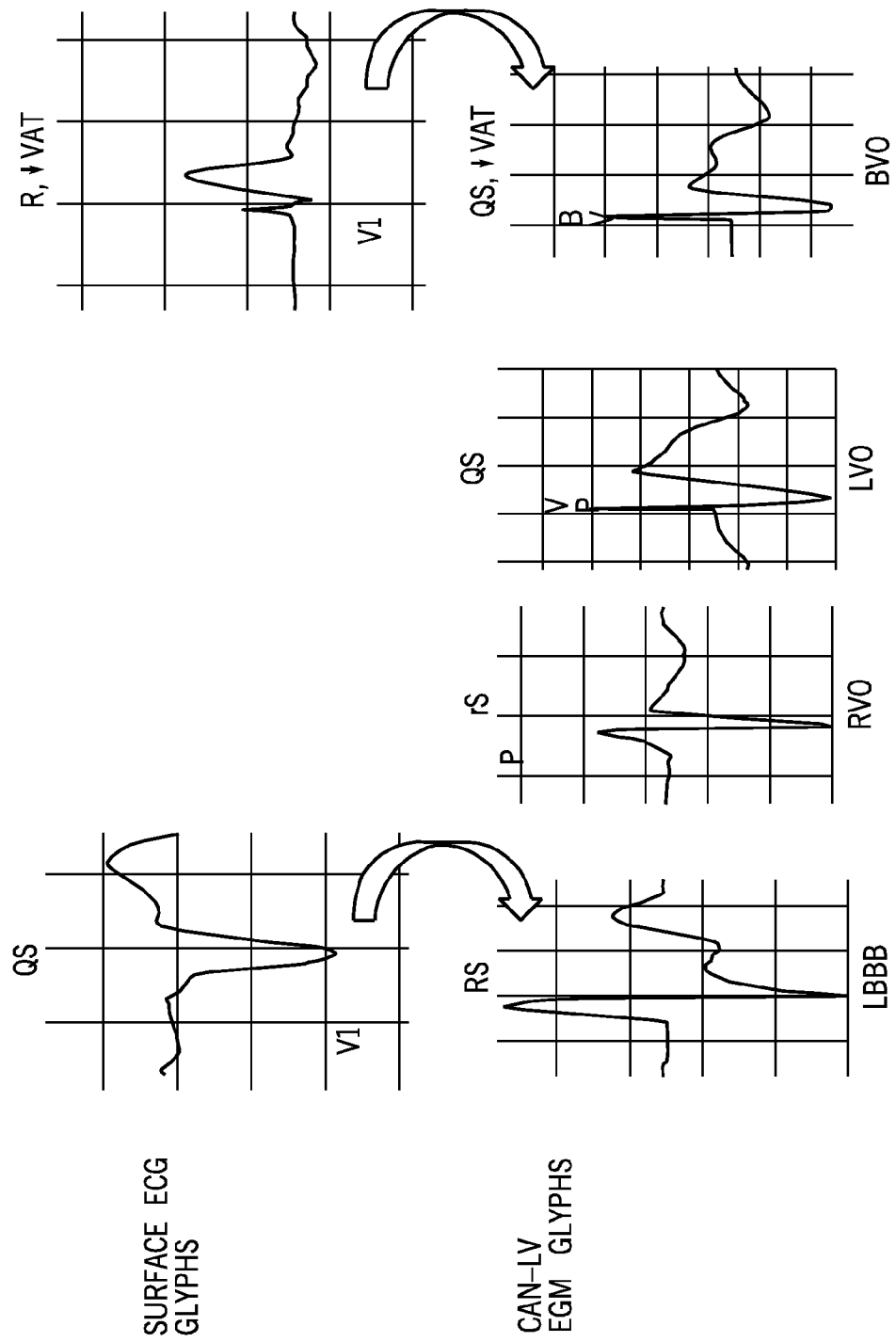
FIG. 25 is a pictorial illustration of CIED-based EGM surrogates for global ventricular activation and ECG-derived fusion response phenotypes during cardiac resynchronization therapy.

An example of CIED-generated electrogram glyph surrogates for surface ECG registration of global ventricular activation is shown in FIG. 25. A typical QS glyph in V1 during LBBB is observed (top row, left). The corresponding Can-LV glyph (for example, local SQ EGM source 2 and LV electrode LV3 or LV3-LV4 pair, etc., in FIG. 24) is RS (bottom row, left). The CIED glyph changes to rS during monochamber RV (RVO) pacing (bottom row, middle) and QS during monochamber LV (LVO) pacing (bottom row, middle). A typical R glyph in V1 (satisfying Oblique Fusion Phenotype) is observed during simultaneous BV (BVO) pacing (top row, right). The corresponding Can-LV glyph is QS (bottom row, right). Note that each condition of LBBB, monochamber, and biventricular pacing yields a unique CIED activation glyph. Note CIED glyph duration is greatest during LVO pacing, which is typical. Note further that the CIED glyph duration is reduced (visibly shorter VAT) for BVO pacing as compared to LBBB, paralleling the changes in VAT reflected in the surface ECG glyphs in pivotal lead V1. In this example, the LV electrode is utilized for both stimulation and EGM recording. It is recognized that alternate combinations of monochamber, cross-chamber, or subcutaneous electrode pairs for either or both purposes of EGM recording and pacing stimulation might yield the optimal CIED glyph surrogates for ECG surface registration of global ventricular activation in the individual patient.

The present invention has been described in terms of one or more preferred embodiments, and it should be appreciated that many equivalents, alternatives, variations, and modifications, aside from those expressly stated, are possible and within the scope of the invention.

What is claimed is:

1. A method for delivering cardiac resynchronization therapy to a patient's heart with a cardiac rhythm management (CRM) device, the steps of the method comprising:
   a) receiving intracardiac signals indicative of cardiac electrical activity in the patient's heart, using electrodes in electrical communication with one of the CRM device and an external programmer, after delivery of electrical impulses to the heart;

b) comparing the received cardiac electrical activity signals with a baseline cardiac electrical activity to characterize ventricular activation patterns using a QRS hieroglyphic framework, the baseline cardiac electrical activity acquired, using electrocardiograph surface leads, before the delivery of electrical impulses to the heart;

c) determining an activation fusion response phenotype based on the comparison in step b), the activation fusion response phenotype corresponding with odds of increased ventricular activation wavefront fusion associated with improved ventricular pump function, the activation fusion response phenotype being differentiated into distinct mutually exclusive phenotypes, including a cancellation fusion response phenotype, an oblique fusion response phenotype, and a summation fusion response phenotype;

d) setting one or more pacing control parameters based on the activation fusion response phenotype determined in step c) and the comparison in step (b); and e) delivering cardiac resynchronization therapy to the patient's heart using the one or more pacing control parameters.

2. The method as recited in claim 1 in which step b) includes identifying one or more QRS complex glyphs in the acquired cardiac electrical activity signals.

3. The method as recited in claim 2 in which step b) further includes comparing the identified QRS complex glyphs with corresponding QRS complex glyphs in the baseline cardiac electrical activity.

4. The method as recited in claim 1 in which step b) further includes comparing a QRS duration in the received cardiac electrical activity signals with a corresponding QRS duration in the baseline cardiac electrical activity.

5. The method as recited in claim 1 in which step c) includes setting at least one of an atrioventricular interval and a ventricular-ventricular interval.

6. The method as recited in claim 1 further comprising characterizing the received signals in step a) as a fusion wavefront comprising propagating wave patterns from multiple cardiac resynchronization therapy stimulation sites.

7. The method as recited in claim 6 further comprising characterizing patterns of wavefront interference in the fusion wavefront based on the propagating wave patterns.

8. The method as recited in claim 1 in which step d) includes setting the one or more pacing control parameters in attempt to change the activation fusion response phenotype when the summation fusion response phenotype is determined in step c).

9. The method as recited in claim 1 further comprising estimating odds of reverse remodeling during cardiac resynchronization therapy based on the comparison in step b) and the determination in step c).

10. The method as recited in claim 9 wherein estimating odds of reverse remodeling during cardiac resynchronization therapy is based on at least one cardiac resynchronization therapy stimulation site.

11. A cardiac implantable electrical device for delivering cardiac resynchronization therapy to a patient's heart, the cardiac implantable electrical device comprising:

an input for receiving intracardiac signals indicative of cardiac electrical activity in the heart;

an impulse delivery system for delivering electrical impulses to the heart to provide cardiac resynchronization therapy thereto;

a memory for storing:
    pacing control parameters for the impulse delivery system, and
    a baseline electrocardiograph electrical activity acquired, using electrocardiograph surface leads, before delivery of electrical impulses delivered to the heart by the impulse delivery system;
and a processor in communication with the memory, the processor being configured to:
    receive intracardiac signals after the delivery of electrical impulses;
    compare the received intracardiac signals to the baseline electrocardiograph electrical activity to characterize ventricular activation patterns using a QRS hieroglyphic framework;
    determine an activation fusion response phenotype based on the comparison, the activation fusion response phenotype corresponding with odds of increased ventricular activation wavefront fusion associated with improved ventricular pump function, the activation fusion response phenotype being differentiated into distinct mutually exclusive phenotypes, including a cancellation fusion response phenotype, an oblique fusion response phenotype, and a summation fusion response phenotype;
    generate adjusted pacing control parameters based on the activation fusion response phenotype and the comparison of the received signals with the baseline electrocardiograph electrical activity; and
    provide cardiac resynchronization therapy to the heart in accordance with the adjusted pacing control parameters.

12. The device of claim 11, wherein QRS complexes in each surface lead of the electrocardiograph are deconstructed into waveform elements, and wherein ventricular activation in each surface lead is characterized by QRS hieroglyphs.

13. The device of claim 12, wherein the processor is further configured to deconstruct the QRS complexes into four possible waveform elements: R, S, Q, and QS.

14. The device of claim 13, wherein the processor is further configured to use amplitudes and durations of the waveform elements of the QRS complexes to characterize specific ventricular activation patterns.

15. The device of claim 14, wherein ventricular activation in each surface lead is characterized by nine possible QRS hieroglyphs:

a. R, when only R-wave is present;
b. RS, when R-wave and S-wave are present with equal amplitude;
c. Rs, when R-wave and S-wave are present, R-wave with greater amplitude;
d. rS, when R-wave and S-wave are present, S-wave with greater amplitude;
e. QS, when Q-wave and S-wave are present with equal amplitude;
f. qR, when Q-wave and R-wave are present, R-wave with greater amplitude;
g. QR, when Q-wave and R-wave are present with equal amplitude;
h. Qr, when Q-wave and R-wave are present, Q-wave with greater amplitude; and
i. QRS, when Q-wave, R-wave, and S-wave are all present.

16. The device of claim 15, wherein the processor is further configured to analyze amplitude, directionality, and time duration of component waveforms of the QRS hieroglyphs to quantify ventricular activation.

17. The device of claim 11, wherein the intracardiac signals serve as morphological surrogates for surface electrocardiograph measures of global cardiac electrical activity.

18. A system for delivering cardiac resynchronization therapy to a patient's heart with a cardiac rhythm management (CRM) device, the system comprising:
  an input configured to be coupled to electrodes in electrical communication with the CRM device to receive intracardiac signals representing cardiac electrical activity in the patient's heart;
  an output configured to communicate operational control parameters to the CRM device; and
  a processor configured to:
    receive the intracardiac signals representing cardiac electrical activity after delivery of electrical impulses to the patient's heart;
    access baseline cardiac electrical activity information, the baseline cardiac electrical activity information acquired, using electrocardiograph surface leads, before the delivery of electrical impulses to the patient's heart;
    compare the intracardiac signals representing cardiac electrical activity with the baseline cardiac electrical activity to characterize ventricular activation patterns using a QRS hieroglyphic framework;
    determine a patient-specific activation fusion response phenotype based on the comparison of the signals representing cardiac electrical activity with the baseline cardiac electrical activity, the activation fusion response phenotype corresponding with odds of increased ventricular activation wavefront fusion associated with improved ventricular pump function, the activation fusion response phenotype being differentiated into distinct mutually exclusive phenotypes, including a cancellation fusion response phenotype, an oblique fusion response phenotype, and a summation fusion response phenotype;
    determine at least one adjusted operational control parameter for controlling pacing using the activation fusion response phenotype and the comparison; and
    communicate the at least one adjusted operational control parameter to the CRM device to perform cardiac resynchronization therapy using the at least one adjusted operational control parameter.

* * * * *